(12) United States Patent
Ma

(10) Patent No.: US 11,986,501 B2
(45) Date of Patent: May 21, 2024

(54) TREATMENT METHODS AND COMPOSITIONS

(71) Applicant: UNM RAINFOREST INNOVATIONS, Albuquerque, NM (US)

(72) Inventor: Thomas Y. Ma, Harrisburg, PA (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 512 days.

(21) Appl. No.: 17/259,889

(22) PCT Filed: Jul. 16, 2019

(86) PCT No.: PCT/US2019/041919
§ 371 (c)(1),
(2) Date: Jan. 12, 2021

(87) PCT Pub. No.: WO2020/018482
PCT Pub. Date: Jan. 23, 2020

(65) Prior Publication Data
US 2021/0290698 A1    Sep. 23, 2021

Related U.S. Application Data

(60) Provisional application No. 62/836,968, filed on Apr. 22, 2019, provisional application No. 62/698,418, filed on Jul. 16, 2018.

(51) Int. Cl.
*A61K 35/745* (2015.01)
*A23L 33/135* (2016.01)
*A61K 35/747* (2015.01)
*A61P 1/16* (2006.01)

(52) U.S. Cl.
CPC .......... *A61K 35/745* (2013.01); *A23L 33/135* (2016.08); *A61K 35/747* (2013.01); *A61P 1/16* (2018.01)

(58) Field of Classification Search
CPC .... A61K 35/745; A61K 35/747; A23L 33/135
See application file for complete search history.

(56) References Cited

U.S. PATENT DOCUMENTS 5,716,615 A * 2/1998 Cavaliere Vesely ... A61K 45/06
                                                      435/252.4
2022/0118031 A1* 4/2022 Kovarik ................. A61Q 15/00

FOREIGN PATENT DOCUMENTS

WO    WO 2014/141075    *  9/2014
WO    WO 2018/109520    *  6/2018

OTHER PUBLICATIONS

Machine translation of Fiore, WO 2014/141075; 47 pages (Year: 2014).*
De Simone et al., Immunopharmacology and immunotoxicology, (1992) vol. 14, No. 1-2, pp. 331-340. (Year: 1992).*
International Patent Application No. PCT/US2019/041919, filed Jul. 16, 2019; International Search Report / Written Opinion, dated Nov. 7, 2019; 9 pages.
International Patent Application No. PCT/US2019/041919, filed Jul. 16, 2019; International Preliminary Report on Patentability, dated Jan. 19, 2021; 6 pages.
Ciorba, "Lactobacillus probiotic protects intestinal epithelium from radiation injury in a TLR-2/cyclo-oxygenase-2-dependent manner", 2012 *Gut Journal*; vol. 61, pp. 829-838.
Dia, "VSL#3 probiotics regulate the intestinal epithelial barrier in vivo and in vitro via the p38 and ERK signaling pathways" Sep. 2011, *International Journal of Molecular Medicine*, vol. 29, pp. 202-208.
Hsieh, "Strengthening of the intestinal epithelial tight junction by Bifidobacterium bifidum", Feb. 12, 2015, *Physiological Reports*, vol. 3(3), pp. 1-17.
Resta-Lenert, "Live probiotics protect intestinal epithelial cells from the effects of infection with enteroinvasive *Escherichia coli* (EIEC)", 2003, *Gut Journal*, vol. 52, pp. 988-997.
Zhang, "A Selected Lactobacillus rhamnosus Strain Promotes EGFR-Independent Akt Activation in an Enterotoxigenic *Escherichia coli* K88-Infected IPEC-J2 Cell Model", Apr. 27, 2015, *PLoS ONE*, vol. 10(4), pp. 1-19.
"Celiac Disease", Celiac Disease: Symptoms & How it's Treated, *Cleveland Clinic*, retrieved Jul. 6, 2023, https://my.clevelandclinic.org/health/diseases/144240-celiac-disease, pp. 1-18.
"Coeliac disease", Coeliac disease—Illnesses & conditions, *NHS inform*, retrieved Jul. 6, 2023, https://www.nhsinform.scot/illnesses-and-conditions/stomach-liver-and-gastronintestinal-tract/coeliac-disease/coeliac-disease, pp. 1-12.
"Coeliac disease" *Wikipedia*, retrieved Jul. 6, 2023, https://en.wikipedia.org/wiki/Coeliac_disease, pp. 1-37.

* cited by examiner

*Primary Examiner* — Brian Gangle
*Assistant Examiner* — Lakia J Jackson-Tongue
(74) *Attorney, Agent, or Firm* — MUETING RAASCH GROUP

(57) ABSTRACT

This disclosure describes compositions and methods involving amounts of probiotic bacteria effective to decrease intestinal permeability or intestinal epithelial tight junction permeability in a subject having or at risk of having defective intestinal barrier, increased intestinal permeability and/or intestinal epithelial tight junction permeability compared to a normal subject. The probiotic bacteria can include a *Lactobacillus* spp. and/or a *Bifidobacterium* spp.

14 Claims, 25 Drawing Sheets

(A)

(B)

(A)

(B)

(A)

(B)

(C)

(A)

(B)

(A)

(B)

(C)

(D)

A    B

TREATMENT METHODS AND COMPOSITIONS

CROSS-REFERENCE TO RELATED APPLICATION

This application is the § 371 U.S. National Stage of International Application No. PCT/US2019/041919, filed Jul. 16, 2019, which claims the benefit of U.S. Provisional Patent Application No. 62/698,418, filed Jul. 16, 2018, and U.S. Provisional Patent Application No. 62/836,968, filed Apr. 22, 2019, each of which is incorporated herein by reference in its entirety.

SUMMARY

This disclosure describes, in one aspect, a composition that includes a probiotic bacterial species that expresses an agonist of TLR2 that causes an increase in aggregation, expression, and/or activity of TLR2. The probiotic bacterial species is provided in an amount effective to cause an enhancement of intestinal epithelial barrier function, decrease intestinal permeability, and/or decreased intestinal epithelial tight junction permeability in a subject having or at risk of having increased intestinal permeability and/or increased intestinal epithelial tight junction permeability compared to a normal subject.

In some embodiments, the probiotic bacterial species can include one or more species of the genus *Lactobacillus*. In some of these embodiments, the *Lactobacillus* species can be *L. acidophilus*. In some of these embodiments, the *Lactobacillus* spp. can be *L. acidophilus* strain ATCC 4356.

In some embodiments, the probiotic bacterial species can include one or more species of the genus *Bifidobacterium*. In some of these embodiments, the *Bifidobacterium* species can be *B. bifidum*. In some of these embodiments, the *Bifidobacterium* spp. can be *B. bifidum* ATCC 35914.

In some embodiments, the composition can include a second probiotic bacterial species.

In some embodiments, the subject further exhibits at least one symptom or clinical sign of an inflammatory condition of the gut. In some of these embodiments, the inflammatory condition of the gut can be Crohn's disease, ulcerative colitis, necrotizing enterocolitis, radiation enteritis, pouchitis, coeliac disease, or irritable bowel syndrome.

In some embodiments, the subject further exhibits at least one symptom or clinical sign of an inflammatory condition of the liver. In some of these embodiments, the inflammatory condition of the liver can be alcoholic liver disease, non-alcoholic fatty liver, non-alcoholic steatohepatitis or metabolic syndrome.

In some embodiments, the subject exhibits at least one symptom or clinical sign of an inflammatory condition of the liver, pancreas, kidney, heart, or the neurological system.

In another aspect, this disclosure describes various methods that involve administering an embodiment of the composition summarized above to a subject. In some embodiments, the composition may be administered in an amount effective to decrease intestinal permeability or intestinal epithelial tight junction permeability. In other embodiments, the composition may be administered in an amount effective to induce an increase in apical membrane aggregation and localization, cell expression and/or activity of TLR2 in intestinal epithelial cells of the subject. In other embodiments, the composition may be administered in an amount effective to induce cytoplasmic to apical membrane translocation of Nod1 or activation of Nod1 in intestinal epithelial cells of the subject. In other embodiments, the composition may be administered in an amount effective to induce an inhibition or suppression of NF-κB activation in intestinal epithelial cells of the subject. In other embodiments, the composition may be administered in an amount effective to induce an increase in occludin gene activity and/or protein expression. In other embodiments, the composition may be administered in an amount effective to ameliorate at least one symptom or clinical sign of an inflammatory condition of the gut. In other embodiments, the composition may be administered in an amount effective to ameliorate at least one symptom or clinical sign of an inflammatory condition of the liver. In other embodiments, the composition may be administered in an amount effective to ameliorate at least one symptom or clinical sign of an inflammatory condition that includes and/or extends beyond the gut and liver.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing or photograph executed in color. Copies of this patent or patent application publication with color drawings or photographss will be provided by the Office upon request and payment of the necessary fee.

Nuclei (blue). Bar=10 μm. (D) *L. acidophilus* adheres to Caco-2 apical membrane surface at sites of TLR2 aggregation (enface view of apical membrane surface). In the absence of LA (LA−), TLR2 is diffusely present in the apical membrane surface. *L. acidophilus* (LA+) causes a rapid increase in apical membrane aggregation and expression of TLR2. *L. acidophilus* attaches at the regions of TLR2 apical membrane aggregation or localization. *L. acidophilus* (green, Dio), TLR2 (red). Bar=5 μm.

Figure 1:
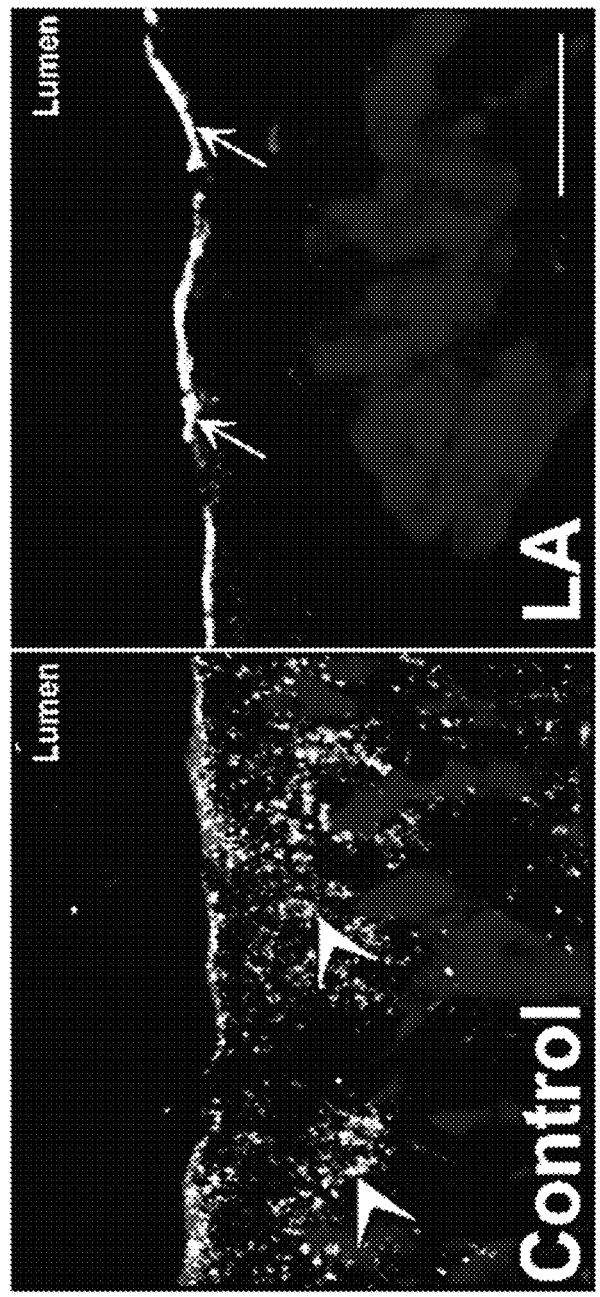
FIG. 1. *Lactobacillus acidophilus* (LA)-induced translocation of Nod1 in mouse intestinal tissue. In the control mouse small intestinal mucosal surface, Nod1 (green) is diffusely present in the cytoplasm of the intestinal epithelial cells. Following *L. acidophilus* (LA) administration (via oral-gastric gavage), there is a rapid (within two hours) cytoplasmic-to-apical membrane translocation of Nod1. Apical actin (red), nucleus (blue), actin/Nod1 co-localization (yellow). White bar=10 μm.
Figure 2:
FIG. 2. Oral-gastric administration of *Bifidobacterium bifidum* (BB) causes cytoplasmic-to-apical membrane translocation of Nod 1 in intestinal epithelial cell in mouse intestinal tissue. (A) In the control mouse small intestinal mucosal surface, Nod1 (green) and Nod2 (not shown) are diffusely present in the cytoplasm of the enterocytes. (B) After *B. bifidum* (BB) administration, there is a rapid (within two hours) cytoplasmic-to-membrane translocation of Nod1. (C) *B. bifidum* administration did not cause membrane translocation of Nod2 (green). Apical actin—red, nucleus—blue, actin/Nod1 co-localization—yellow. White bar=10 μm.
Figure 3:
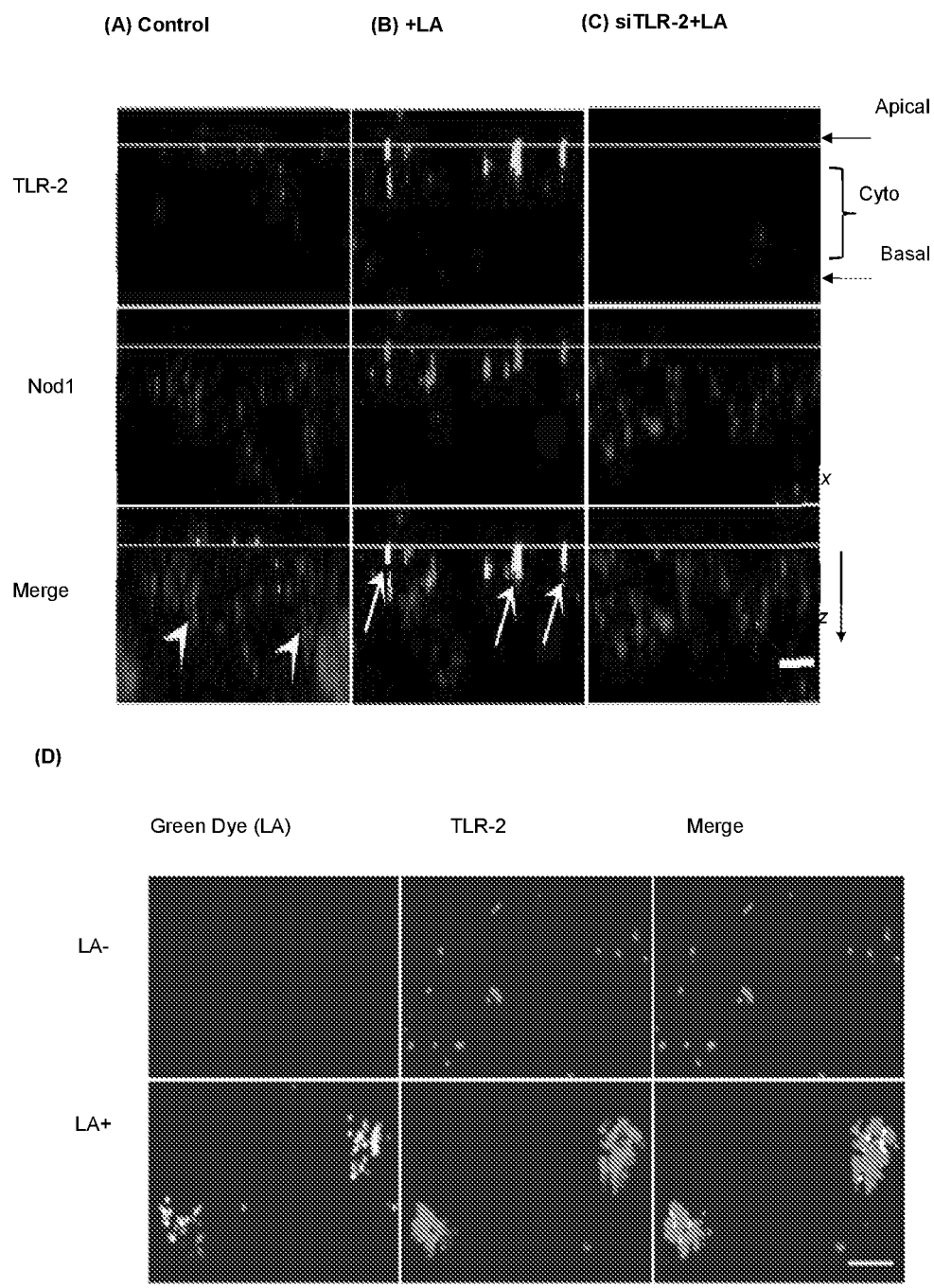
FIG. 3. *L. acidophilus* causes cytoplasmic-to-apical membrane translocation of Nod 1 in a TLR2-dependent manner in Caco-2 intestinal epithelial cells. Caco-2 intestinal epithelial cell Nod1 (red) and TLR2 (green) cellular localization as seen in x-z plane (confocal imaging) along the apical-to-basal axis. (A) In control Caco-2 cells, TLR2 is diffusely present in the apical membrane and Nod-1 is diffusely present in the cytoplasm (arrowhead). (B) *L. acidophilus* (LA) induces a rapid increase in apical membrane aggregation and expression of TLR2 and cytoplasmic-to-apical membrane translocation of Nod1. Nod1 co-localizes with TLR2 (yellow) (arrows). (C) SiRNA knock-down of TLR2 inhibits apical membrane translocation of Nod1.
Figure 4:
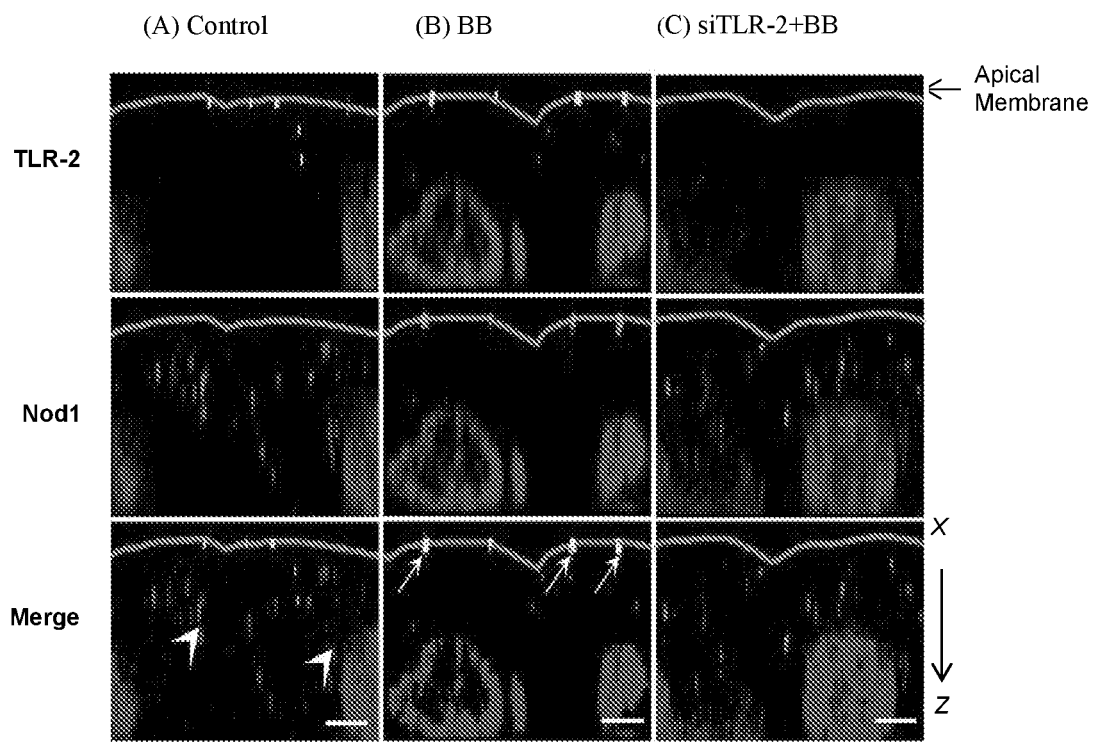
Figure 4:
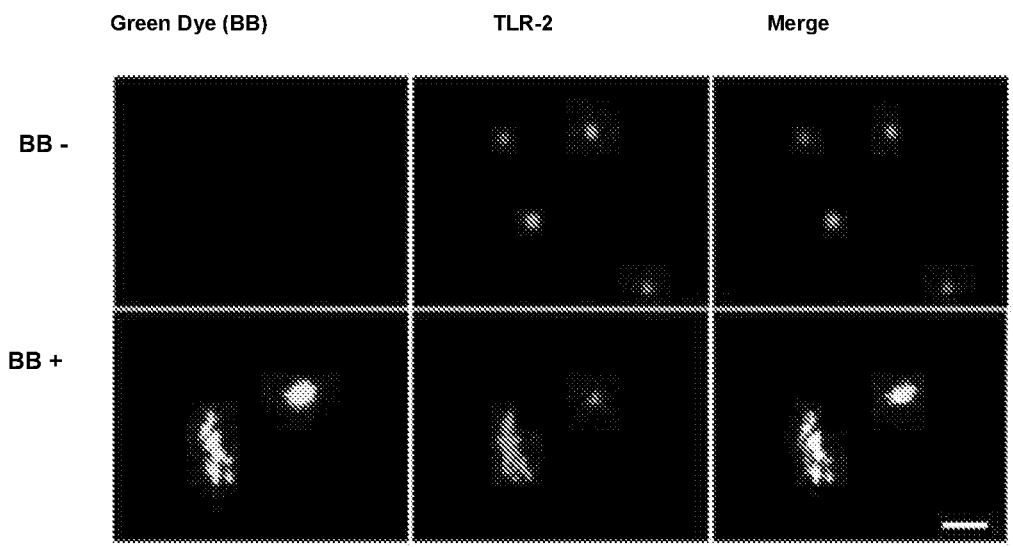

FIG. 4. *B. bifidum* causes cytoplasmic-to-apical membrane translocation of Nod 1 in Caco-2 intestinal epithelial cells in a TLR2 dependent manner. Caco-2 Nod1 (red) and TLR2 (light green) cellular localization as seen in x-z plane along the apical-to-basal axis in confocal imaging. The apical membrane is outlined in purple color. (A) In control Caco-2 cells, TLR2 is sparsely and diffusely present in apical membrane and Nod1 diffusely in the cytoplasm (arrowhead). (B) *B. bifidum* induces an increase in apical membrane aggregation and expression of TLR2 and cytoplasmic-to-apical membrane translocation of Nod1. Nod1 co-localizes with TLR2 (yellow) (arrows). (C) SiRNA KD of TLR2 inhibits the membrane translocation of Nod1. Nuclei (blue). Bar=10 μm. (D) *B. bifidum* adheres to Caco-2 apical membrane at the sites of TLR2 aggregations (en-fâce view of apical membrane surface). BB (green, Dio), TRL-2 (red). Bar=5 μm.

Figure 5:
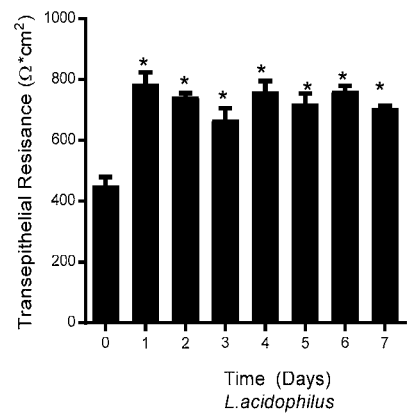
Figure 5:
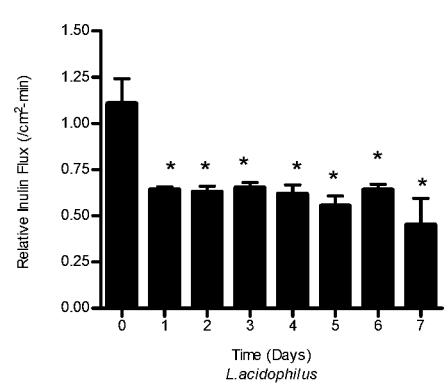

FIG. 5. Time course effects of *L. acidophilus*. (A) Time course effect of *L. acidophilus* ($10^8$ CFU/ml) on Caco-2 TER. (B) Time course effect of *L. acidophilus* ($10^8$ CFU/ml) on mucosal-to-serosal flux of paracellular marker inulin.

Figure 6:
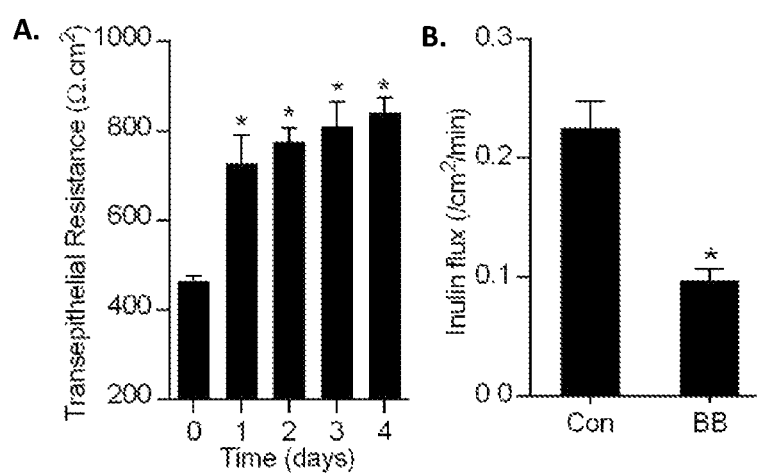

FIG. 6. Time course effect of *B. bifidum*. (A) Time course effect of *B. bifidum* ($10^8$ CFU/ml) on Caco-2 TER. (B) Time course effect of *B. bifidum* ($10^8$ CFU/ml) on apical-to-basal flux of paracellular marker inulin (24 hours).

Figure 7:
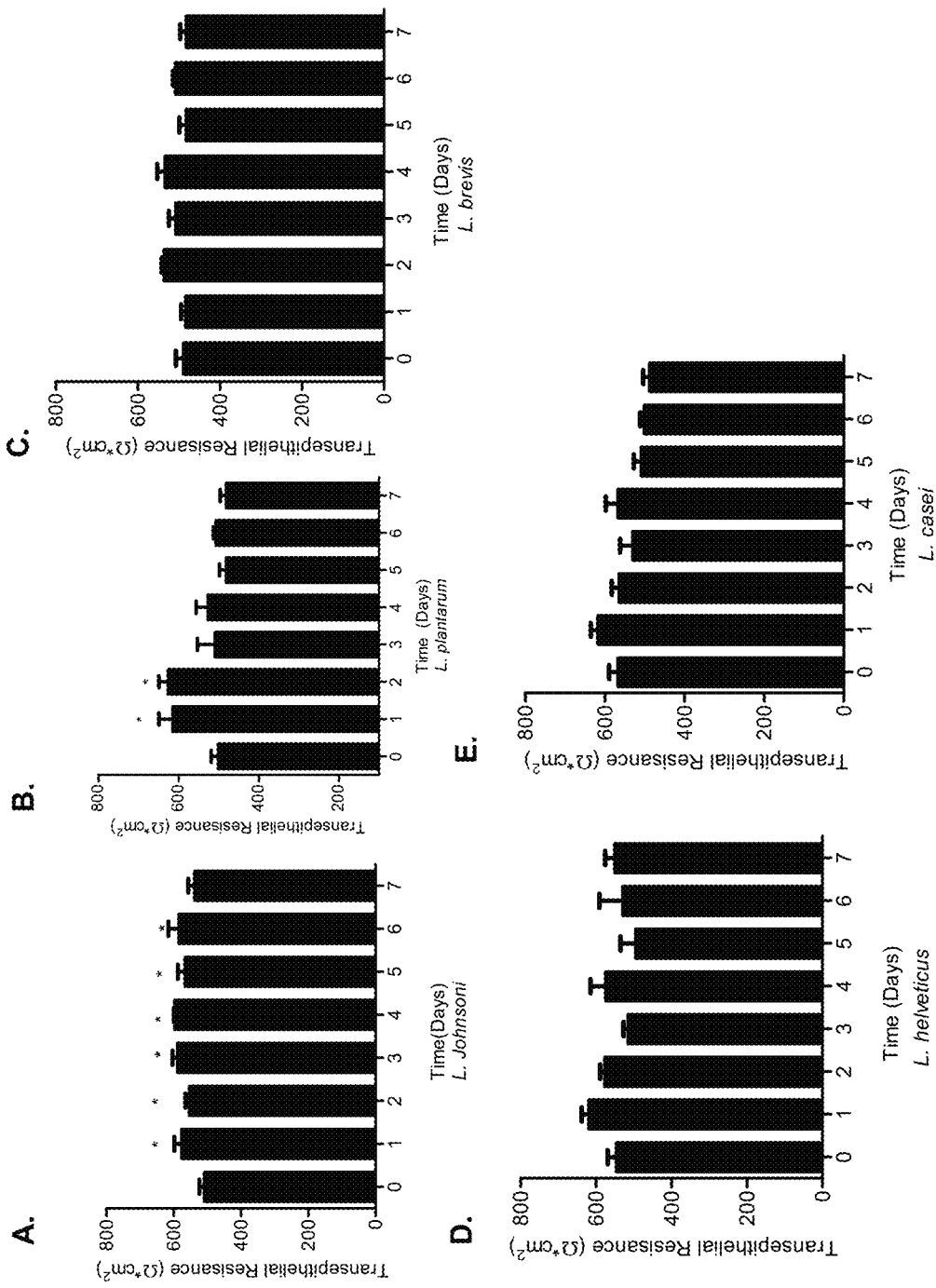

FIG. 7. Time course effect of different species of *Lactobacillus* ($10^8$ CFU/ml) on Caco-2 TER. (A) *L. jonhsoni* (B) *L. plantarum* (C) *L. brevis* (D) *L. helveticus*, (E) *L. casei*. *L. jonhsoni* and *L. plantarum* caused a transitory increase in TER.

Figure 8:
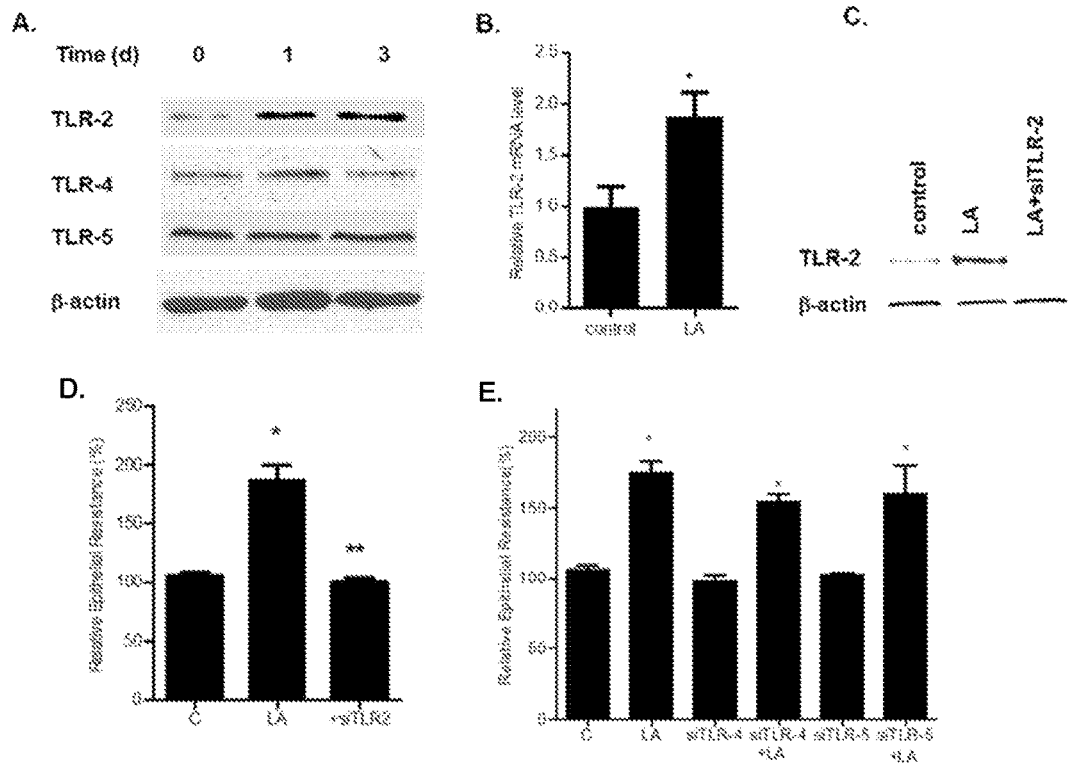

FIG. 8. Effect of LA on expression of TLR2, TLR4, and TLR5 in filter-grown Caco-2 cells. (A) LA ($10^8$ CFU/ml) caused an increase in TLR2 protein expression in Caco-2 monolayers, but not TLR4 or TLR5 expression. (B) LA also caused an increase in TLR2 mRNA expression in Caco-2 monolayers as assayed by real-time PCR. (C) The TLR2 siRNA transfection caused a near-complete depletion of TLR2 in filter-grown Caco-2 monolayers. (D) The siRNA induced knockdown of TLR2 expression completely inhibited the LA induced increase in Caco-2 TER. (E) The siRNA-induced knock down of TLR4 and TLR5 did not inhibit the LA induced increase in Caco-2 TER.

Figure 9:
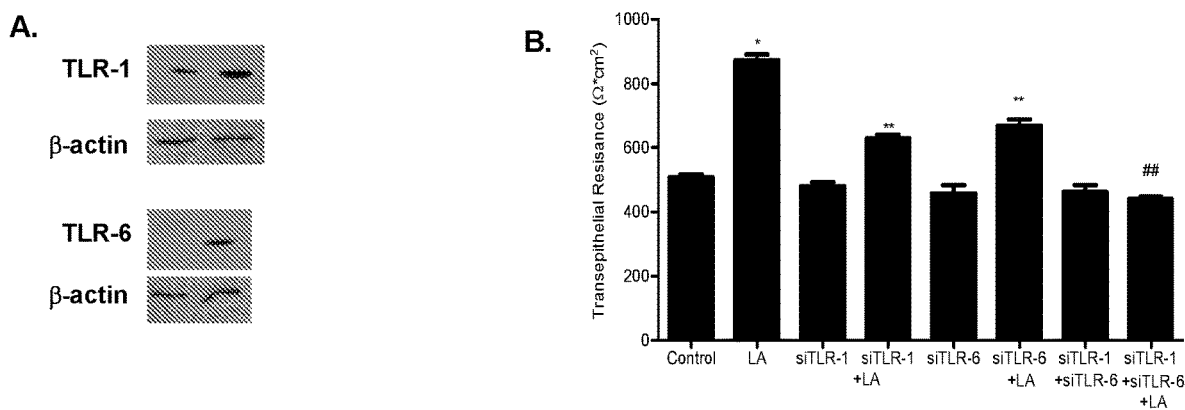

FIG. 9. LA causes an increase in TLR1 and TLR6 protein expression. (A) Effect of *L. acidophilus* on Toll-like receptor TLR1 and TLR6 expression in filter grown Caco-2 monolayers. (B) Effect of TLR1 or TLR6 siRNA transfection on *L. acidophilus* induced increase in Caco-2 TER (B). The siTLR1 or siTLR6 transfection caused a partial inhibition of LA induced increase in Caco-2 TER; the combination of siTLR1 and siTLR6 transfection completely inhibited the LA induced increase in TER.

Figure 10:
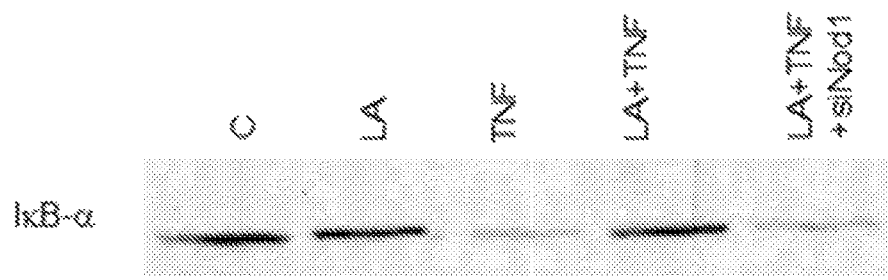
Figure 10:
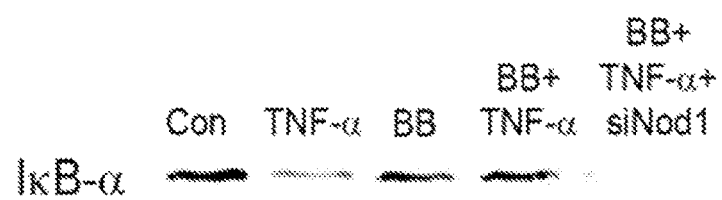

FIG. 10. Effect of treatment with probiotic species on IκB-degradation. (A) *L. acidophilus*; (B) *B. bifidum*.

Figure 11:
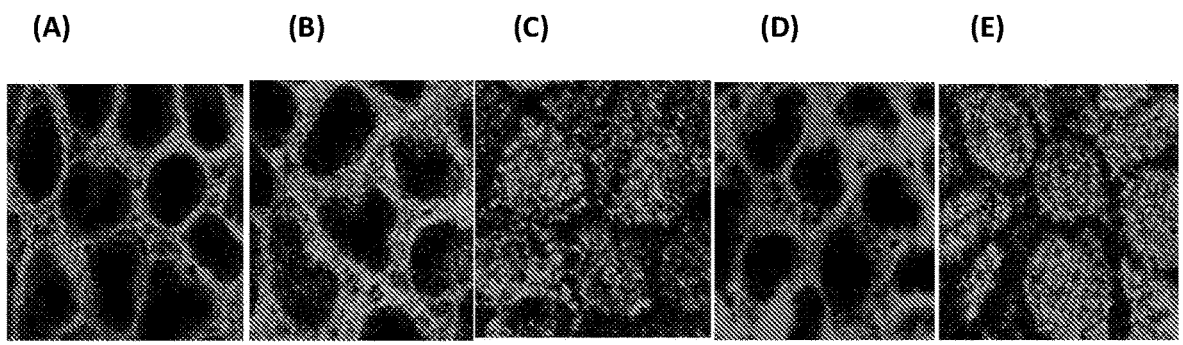

FIG. 11. Effect of *L. acidophilus* treatment on TNF-α-induced nuclear translocation and activation of NF-κBp65. (A) In the control Caco-2 cells, NF-κBp65 (red) is present in the cytoplasm of Caco-2 cells outside the nucleus. (B) *L. acidophilus*-treated Caco-2 cells. (C) TNF-α caused a rapid activation and cytoplasmic-to-nuclear translocation of NF-κBp65 in Caco-2 cells (Red). (D) *L. acidophilus* completely suppressed TNF-α-induced p65 nuclear translocation.

(E) SiRNA knockdown of Nod1 reversed *L. acidophilus* suppression of p65 nuclear translocation.

Figure 12:
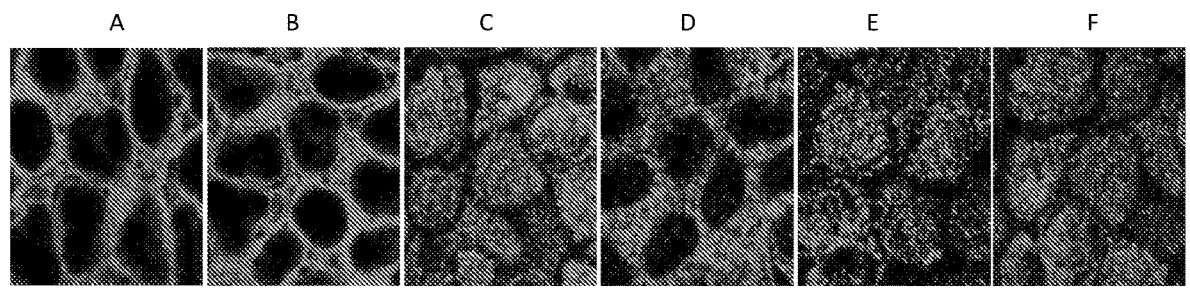

FIG. 12. Effect of *B. bifidum* treatment on Caco-2 nuclear translocation of NF-κBp65. (A) In the control Caco-2 cells, NF-κBp65 (red) is present in the cytoplasm of Caco-2 cells outside the nucleus. (B) *B. bifidum*-treated Caco-2 cells. (C) TNF-α caused a rapid activation and cytoplasmic-to-nuclear translocation of NF-κBp65 (red). (D) *B. bifidum* suppressed the TNF-α-induced p65 nuclear translocation. (E) SiRNA knockdown of Nod1 reversed the *B. bifidum* suppression of p65 activation. (F) SiRNA knockdown of PPAR-γ reversed the *B. bifidum* suppression of p65 activation.

Figure 13:
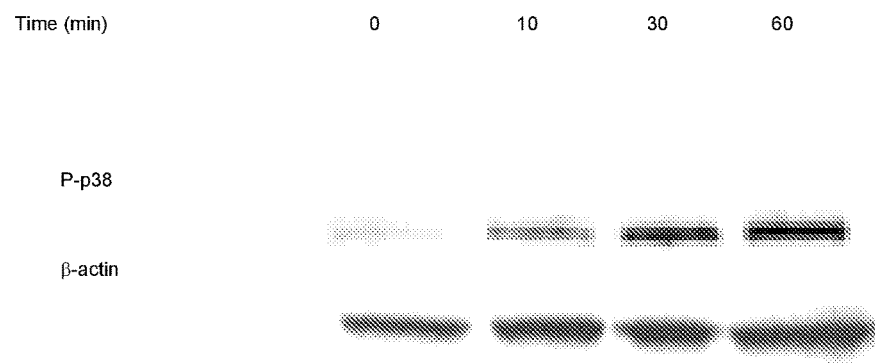

FIG. 13. Time course effect of *L. acidophilus* on phosphorylation of p38 kinase.

Figure 14:
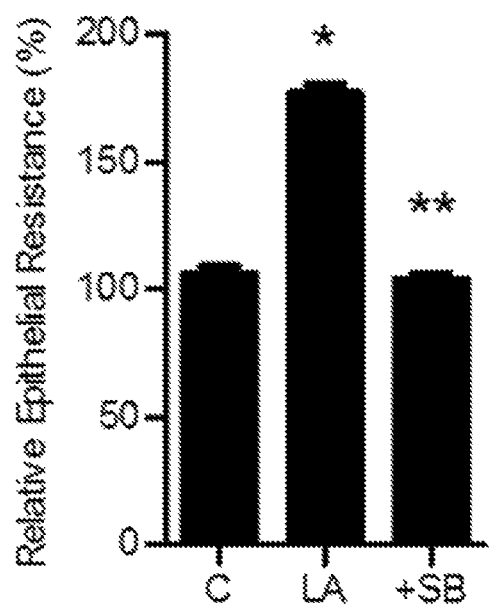

FIG. 14. P38 kinase inhibitor SB-203580 inhibited the *L. acidophilus*-induced increase in Caco-2 TER.

Figure 15:
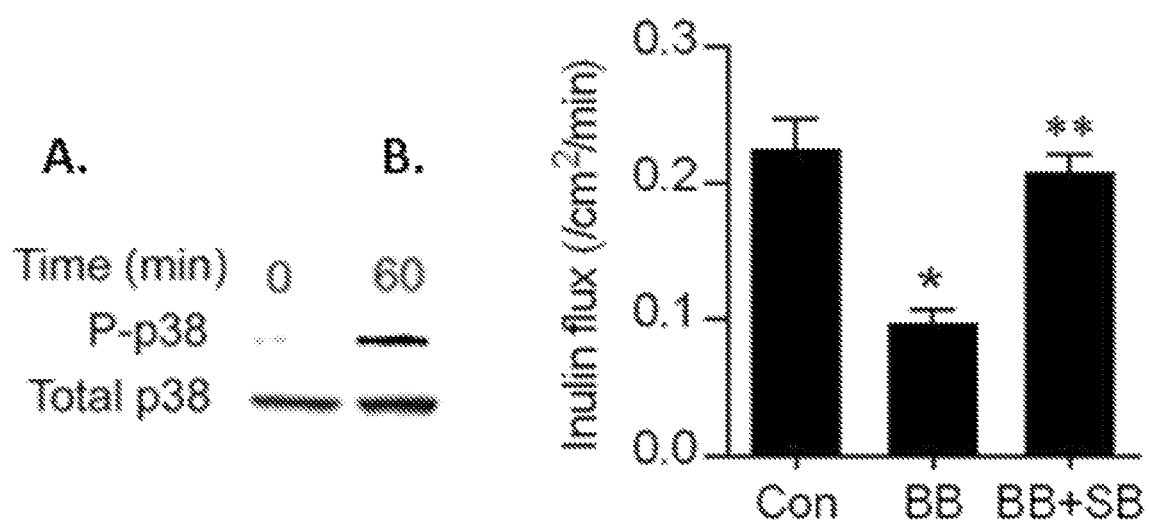

FIG. 15. Effects of *B. bifidum*-treatment on phosphorylation of p38 kinase. (A) Time course effect of *B. bifidum* on phosphorylation of p38 kinase. (B) P38 kinase inhibitor SB-203580 inhibited the *B. bifidum*-induced decrease in Caco-2 inulin flux.

Figure 16:
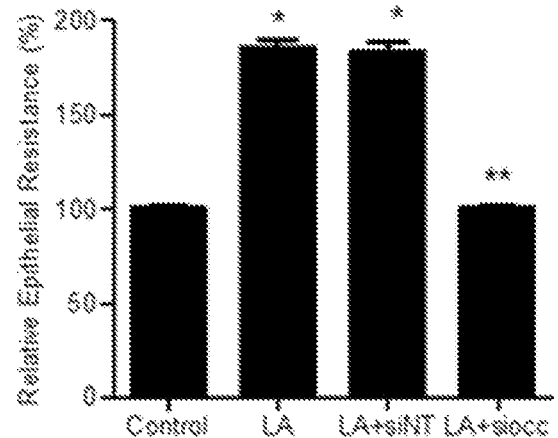

FIG. 16. Effects of *L. acidophilus* treatment on occludin protein expression. (A) *L. acidophilus* causes an increase in occludin protein expression. (B) siRNA knockdown of occludin inhibited the *L. acidophilus*-induced increase in Caco-2 epithelial resistance.

Figure 17:
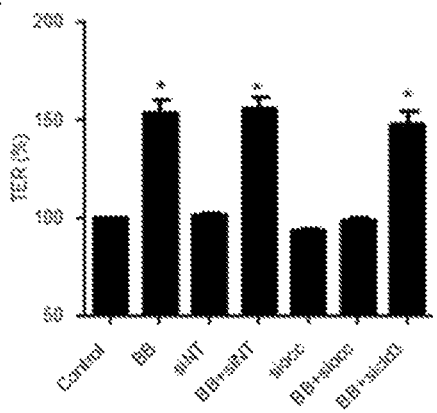

FIG. 17. Effects of *B. bifidum* treatment on expression of occludin and claudin-3. (A) *B. bifidum* caused an increase in Caco-2 occludin and claudin-3 expression. (B) The siRNA knockdown of occludin inhibited the *B. bifidum*-induced increase in occludin expression. The siRNA knockdown of occludin did not inhibit the *B. bifidum*-induced increase in claudin-3 expression. NT=non-target.

Figure 18:
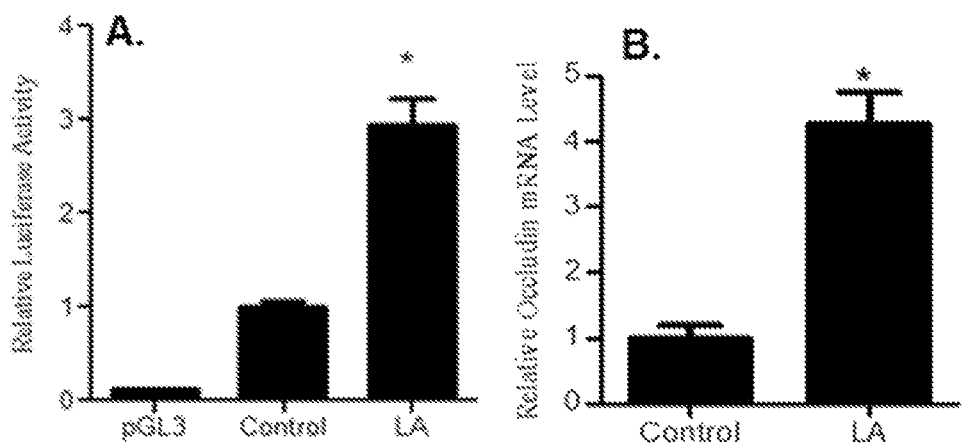

FIG. 18. Effects of *L. acidophilus* treatment on occludin expression. (A) *L. acidophilus* causes an increase in occludin promoter activity as assessed by luciferase activity (reporter gene) following transfection of Caco-2 monolayers with PGL3 plasmid vector encoding the occludin promoter region. (B) *L. acidophilus* causes an increase in occludin mRNA expression. pGL3: vector alone; control: full length 2023 bp occludin promoter.

Figure 19:
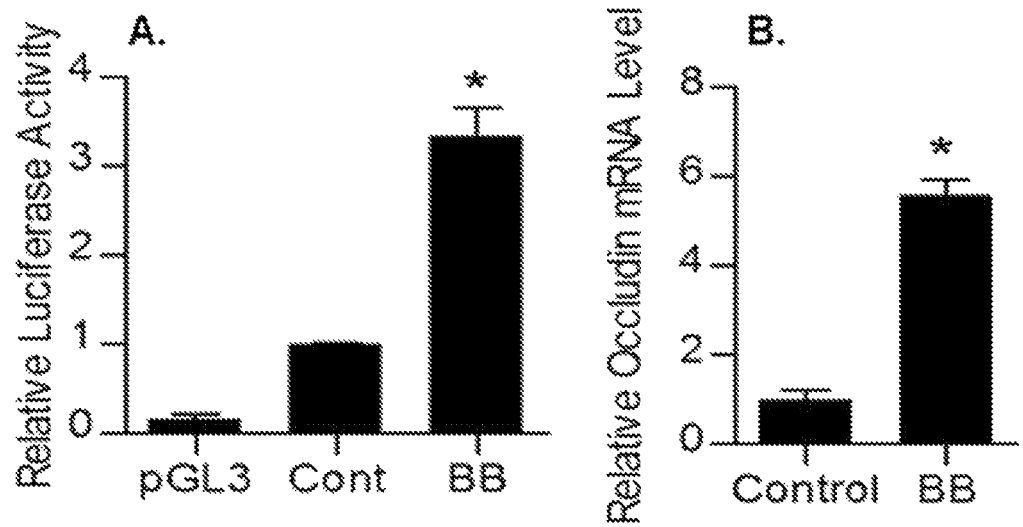

FIG. 19. Effects of *B. bifidum* treatment on occludin expression. (A) *B. bifidum* causes an increase in occludin promoter activity in Caco-2 monolayers. (B) *B. bifidum* causes an increase in occludin mRNA expression in Caco-2 monolayers.

Figure 20:
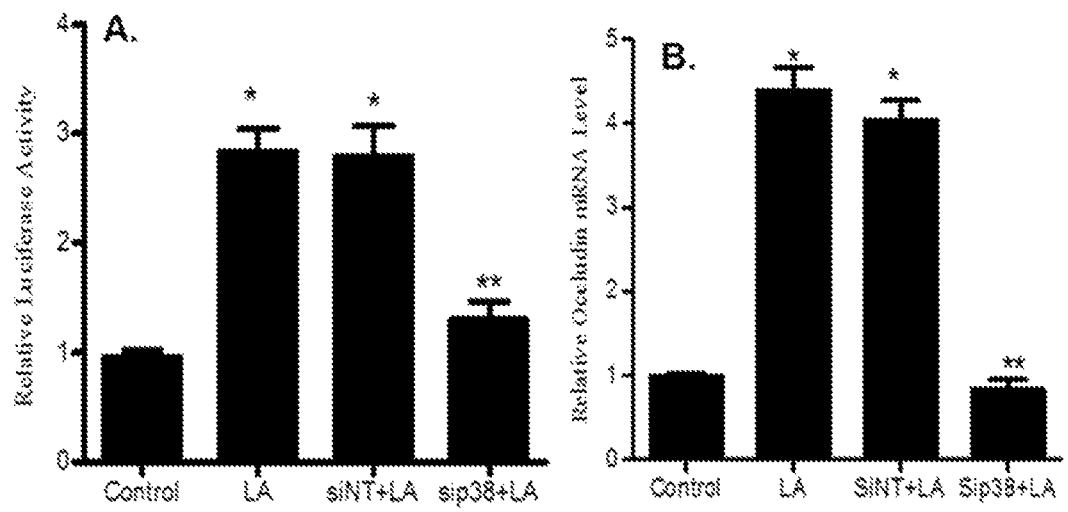

FIG. 20. Inhibition of *L. acidophilus*-induced increase in occludin expression. (A) siRNA-induced knockdown of p38 kinase inhibited the *L. acidophilus*-induced increase in occludin promoter activity in Caco-2 monolayers. (B) siRNA-induced knockdown of p38 kinase inhibited the *L. acidophilus*-induced increase in occludin mRNA levels.

Figure 21:
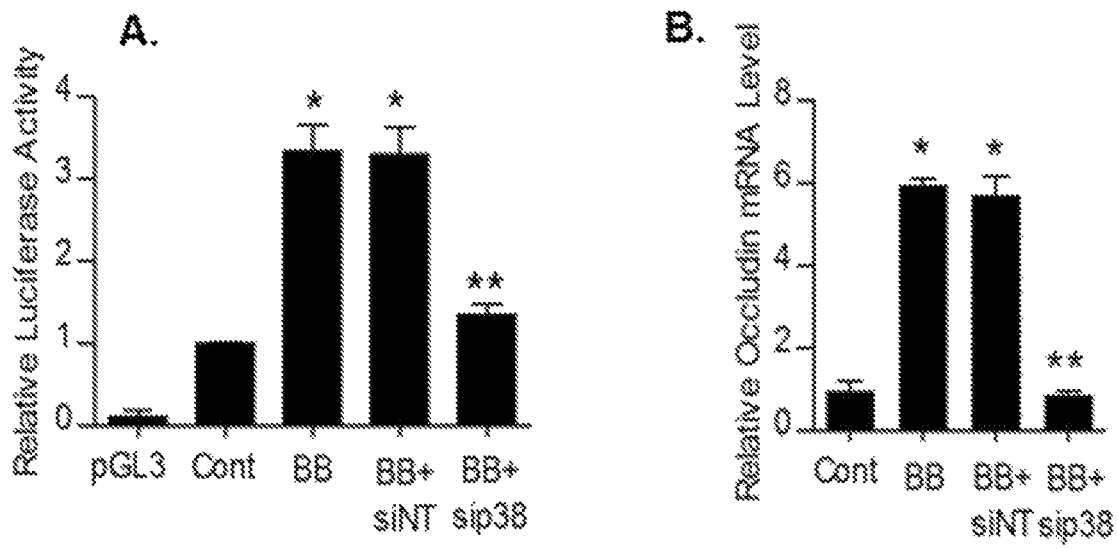

FIG. 21. Inhibition of *B. bifidum*-induced increase in occludin expression. (A) siRNA-induced knockdown of p38 kinase inhibited the *B. bifidum*-induced increase in occludin promoter activity in Caco-2 monolayers. (B) siRNA-induced knockdown of p38 kinase inhibited the *B. bifidum*-induced increase in occludin mRNA levels.

Figure 22:
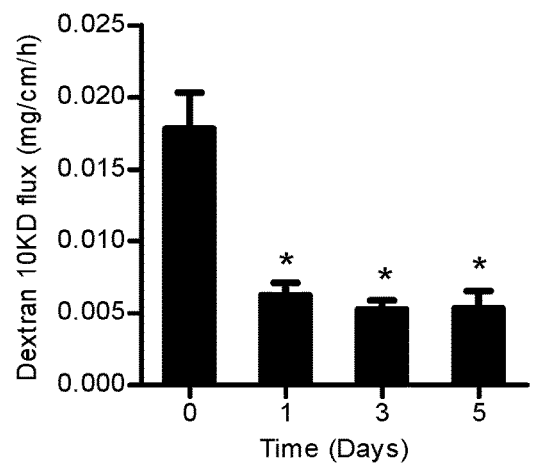
Figure 22:
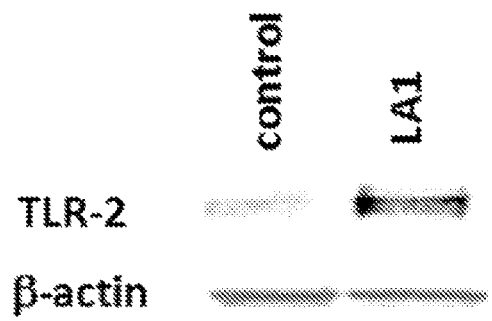
Figure 22:
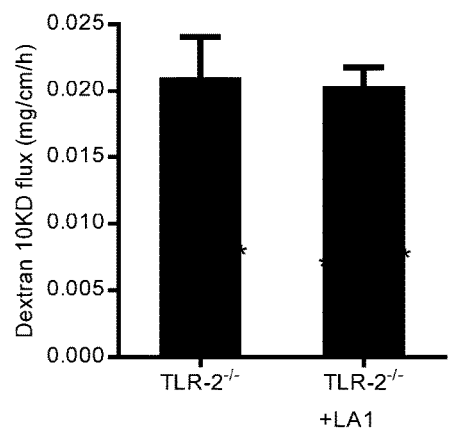

FIG. 22. *L. acidophilus*-induced decrease in small intestinal permeability is mediated through TLR2. (A) Oral-gastric administration of *L. acidophilus* ($10^9$ CFU/ml) causes a decrease in mouse small intestinal permeability as measured by FITC-labeled 10 KD dextran. (B) *L. acidophi-*

*lus* caused an increase in TLR2 expression in the mouse small intestinal tissue. (C) The *L. acidophilus*-induced decrease in small intestinal permeability was inhibited in mice deficient in TRL2 expression (TLR2$^{-/-}$). (n=3-5 mice).

Figure 23:
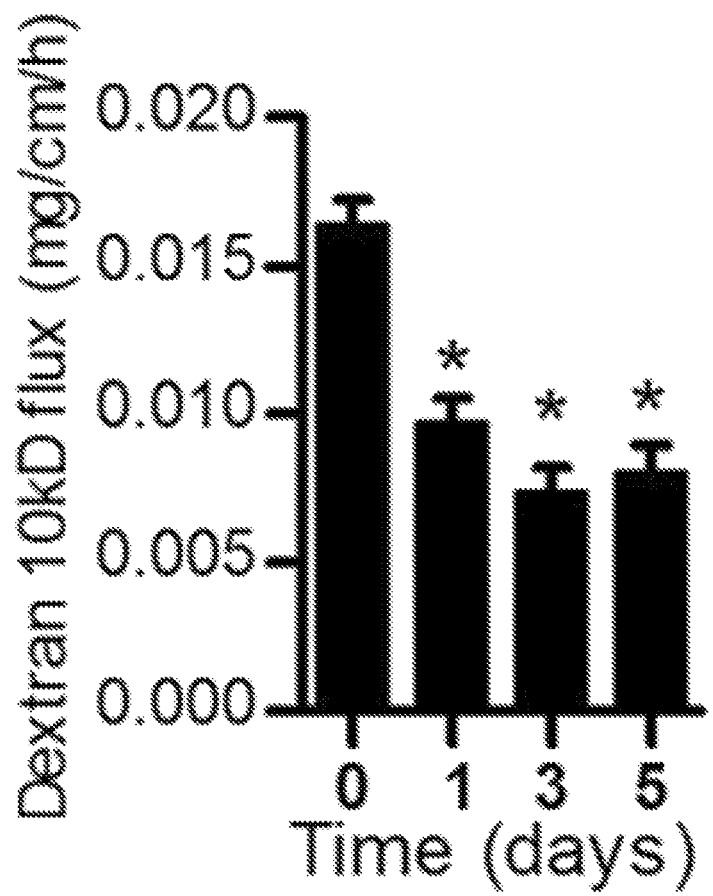

FIG. 23. Oral-gastric administration of *B. bifidum* ($10^9$ CFU/ml) caused a decrease in mouse small intestinal permeability.

Figure 24:
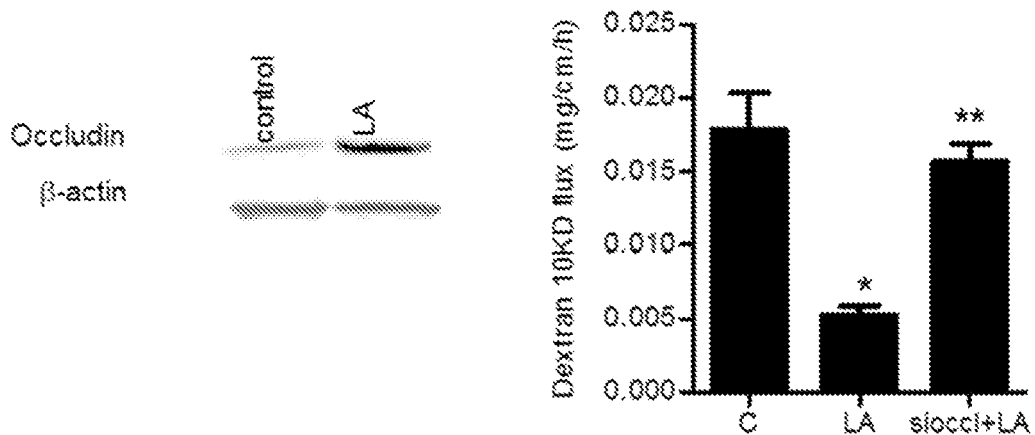

FIG. 24. *L. acidophilus* effects on occludin expression in small intestinal tissue. (A) *L. acidophilus* caused an increase in occludin protein expression in small intestinal tissue. (B) The siRNA-induced knockdown of enterocyte occludin in vivo inhibited the *L. acidophilus*-induced decrease in small intestinal permeability. (n=3-5 mice).

Figure 25:
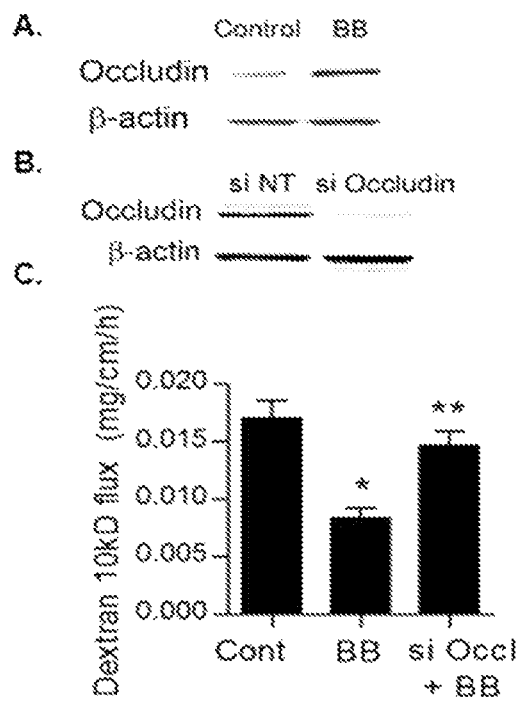

FIG. 25. *B. bifidum* effects on occludin expression in small intestinal tissue. (A) *B. bifidum* causes an increase in occludin protein expression in small intestine tissue. (B) Effect of siRNA knockdown of occludin in mouse small intestinal tissue. (C) The siRNA-induced knockdown of occludin in mouse small intestinal cells in vivo inhibited the *B. bifidum*-induced decrease in mouse small intestinal permeability. (n=3-5 mice).

Figure 26:
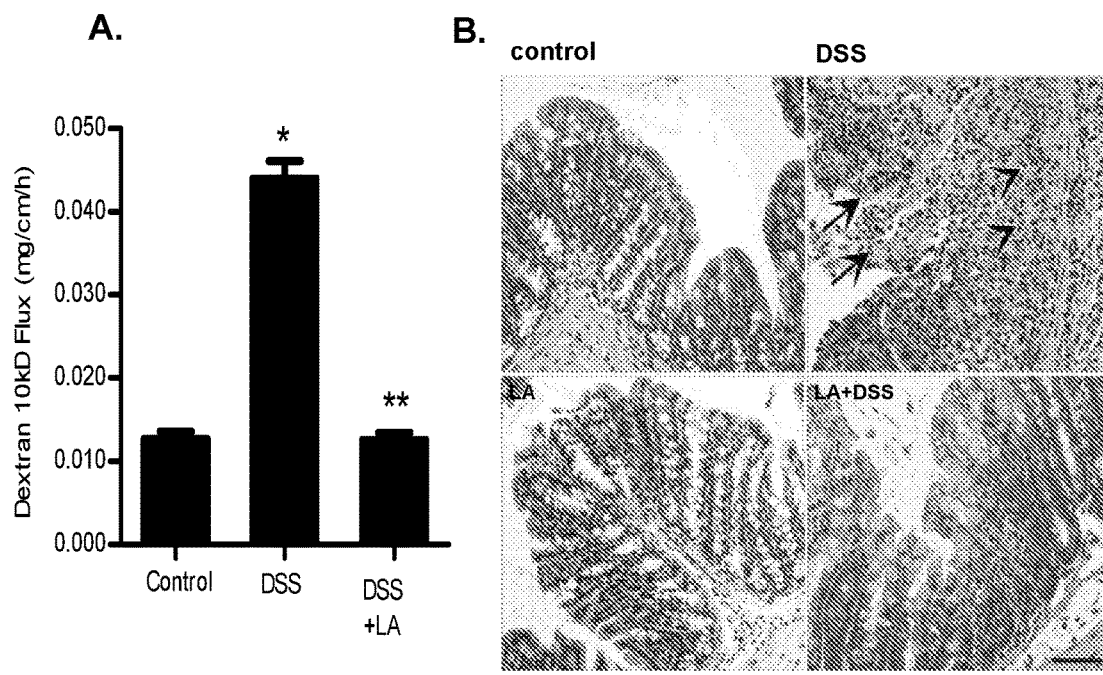

FIG. 26. *L. acidophilus* effect on colonic permeability. (A) *L. acidophilus* inhibited DSS-induced increase in colonic permeability. (B) *L. acidophilus* attenuated or inhibited the DSS-induced increase in colonic inflammation, characterized by mucosal ulceration (arrows) and diffuse infiltration of inflammatory cells (arrowheads). H&E, bar=50 µm. (n=3-5 mice). *L. acidophilus* (LA) administration was started two days before DSS administration and continued throughout the seven days of daily DSS administration.

Figure 27:
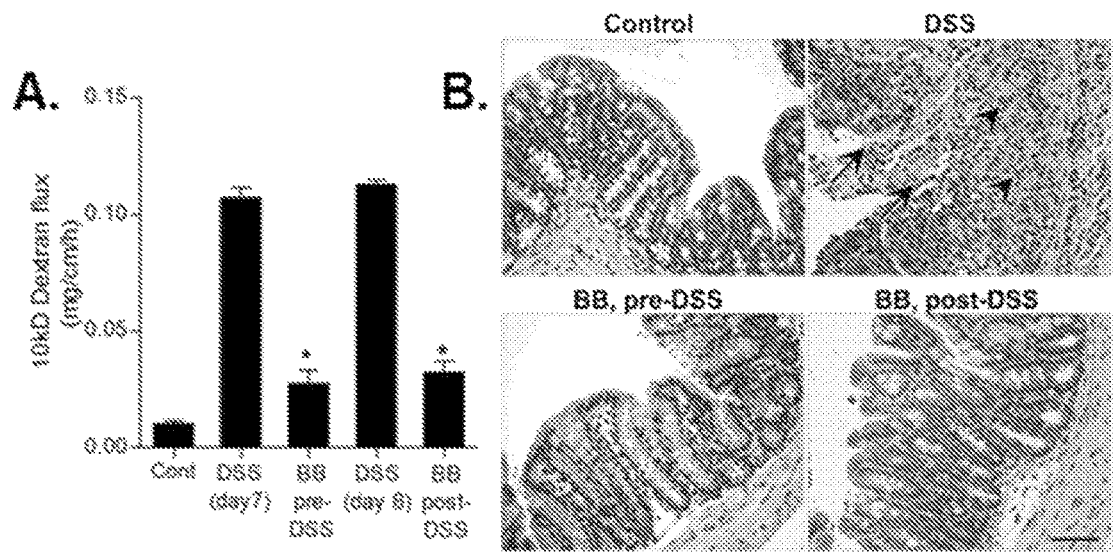

FIG. 27. *B. bifidum* effect on colonic permeability. (A) DSS-induced increase in mouse colonic permeability. (B) DSS-induced increase in mouse colonic inflammation. Mucosal ulceration (arrow) and diffuse infiltration of inflammatory cells (arrowheads) were inhibited by *B. bifidum* pre-treatment starting two days before DSS administration and continuing through DSS administration for seven days; BB, pre-DSS) and was healed by *B. bifidum* therapy (starting at Day 5 of DSS administration and continuing to Day 8 of DSS; BB, post-DSS). bar=50 µm.

Figure 28:
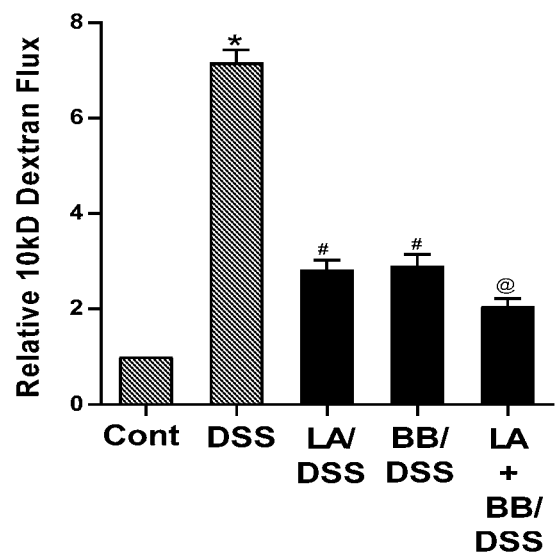
Figure 28:
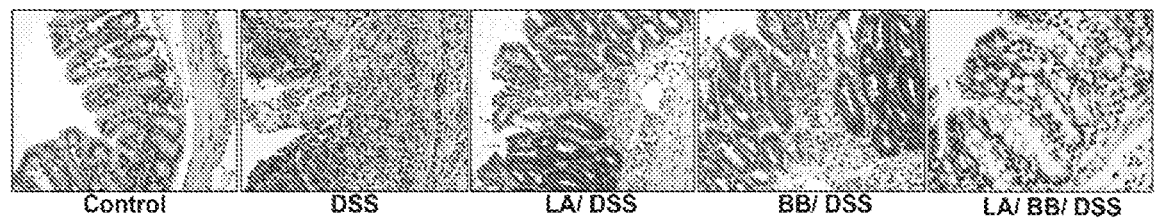

FIG. 28. Effects of treatment with a combination of *L. acidophilus* and *B. bifidum*. (A) *L. acidophilus* and *B. bifidum* combination caused a greater maintenance and therapeutic repair against DSS-induced increase in colonic permeability. (B) *L. acidophilus* and *B. bifidum* combination caused a greater maintenance and therapeutic repair against DSS-induced colitis. The DSS-induced increase in mouse intestinal permeability and colitis was inhibited to a significantly greater extent by LA+BB pre-treatment (starting two days before DSS and continuing through DSS administration for seven days; LA+BB, pre-DSS) and was also repaired or healed to a significantly greater extent by combined LA+BB therapy (starting at Day 5 of DSS administration and continuing to Day 8 of DSS; LA/BB/DSS). bar=50 µm.

Figure 29:
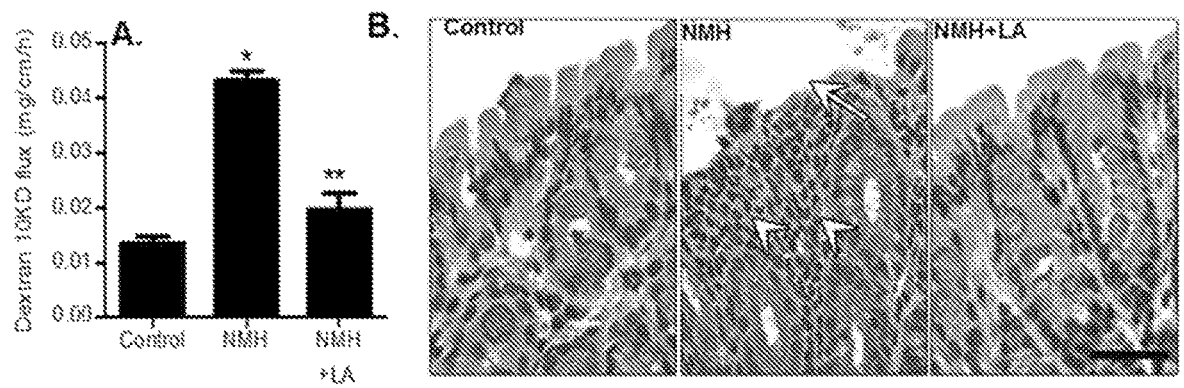

FIG. 29. Effect of chronic administration of *L. acidophilus*. (A) Chronic administration of *L. acidophilus* inhibited the increase in intestinal permeability in IL-10$^{-/-}$ mice raised in normal microbial housing. (B) Chronic administration of *L. acidophilus* inhibited the increase in the development of intestinal inflammation in IL-10$^{-/-}$ mice raised in normal microbial housing. Note denudation of epithelial lining (arrow) and infiltration of inflammatory cells (arrowheads).

Figure 30:
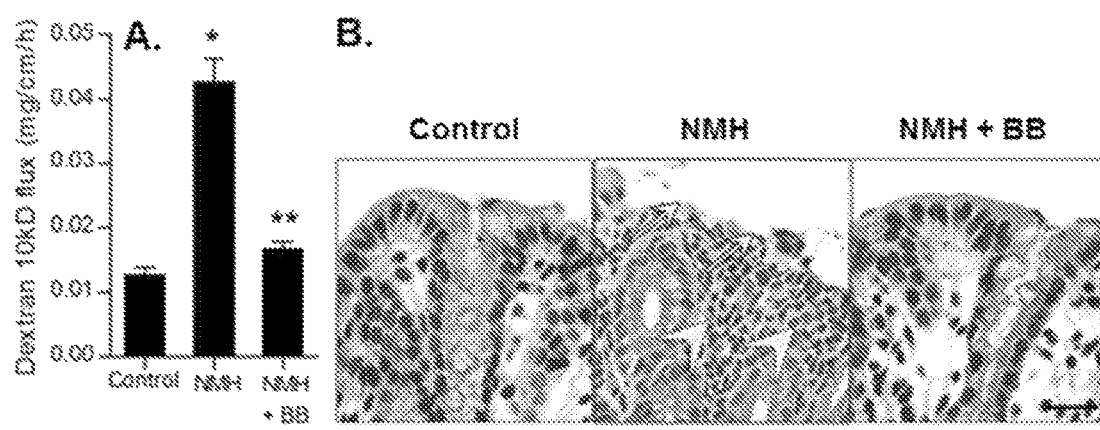

FIG. 30. Effect of chronic administration of *B. bifidum*. (A) Chronic administration of *B. bifidum* inhibited the increase in intestinal permeability in IL-10$^{-/-}$ mice raised in normal microbial housing. (B) Chronic administration of *B. bifidum* inhibited the increase in the development of intestinal inflammation in IL-10$^{-/-}$ mice raised in normal microbial housing. Note denudation of epithelial lining (arrow) and infiltration of inflammatory cells (arrowheads).

Figure 31:
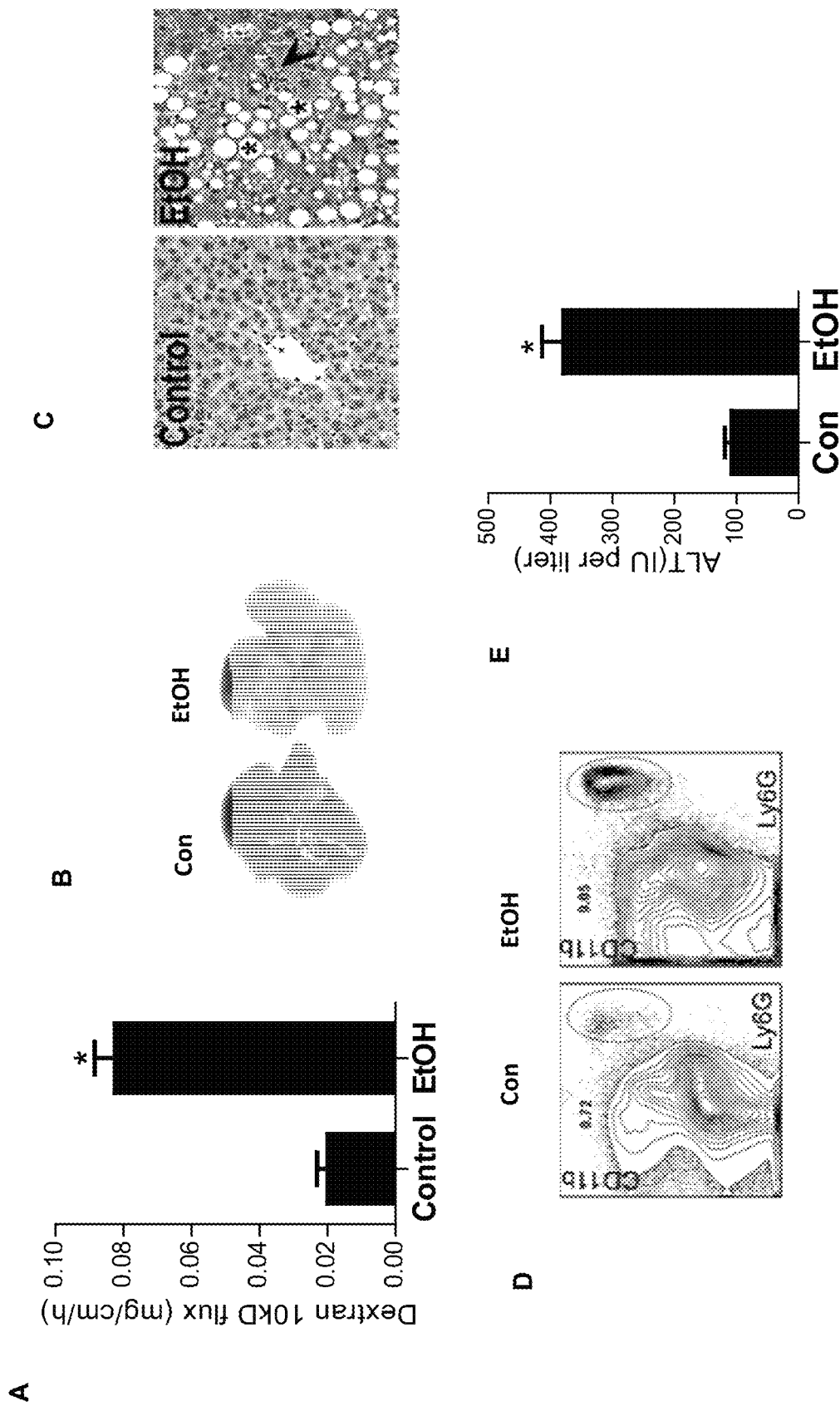

FIG. 31. Effects of chronic ethanol (EtOH) feeding and binge (F+B). (A) Mouse intestinal permeability (10 KD dextran flux); (B) gross appearance of the liver; (C) liver histology (H & E stain, 400×; arrow: PMN infiltrate); (D) flow cytometry showing increase in CD11b/Ly6G (circled areas) PMNs in liver tissue in EtOH-fed mice; (E) serum ALT levels. (*p<0.01 vs. control). Mice were fed alcohol daily (5% v/v, 1 ml) for 10 days, followed by a binge (5 g/Kg BW) on the 11th day.

Figure 32:
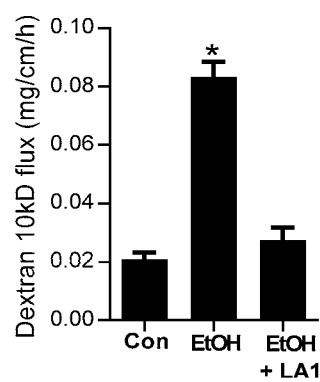
Figure 32:
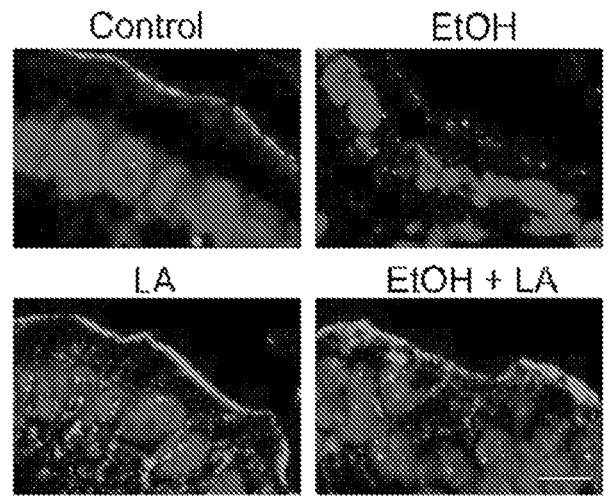
Figure 32:
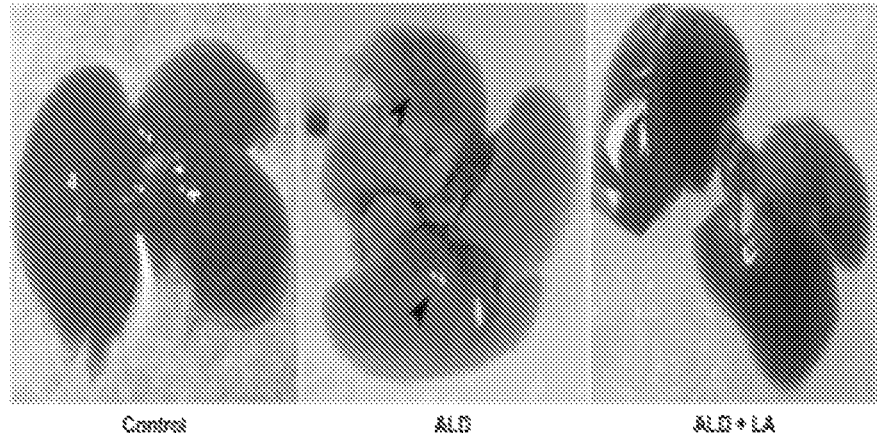
Figure 32:
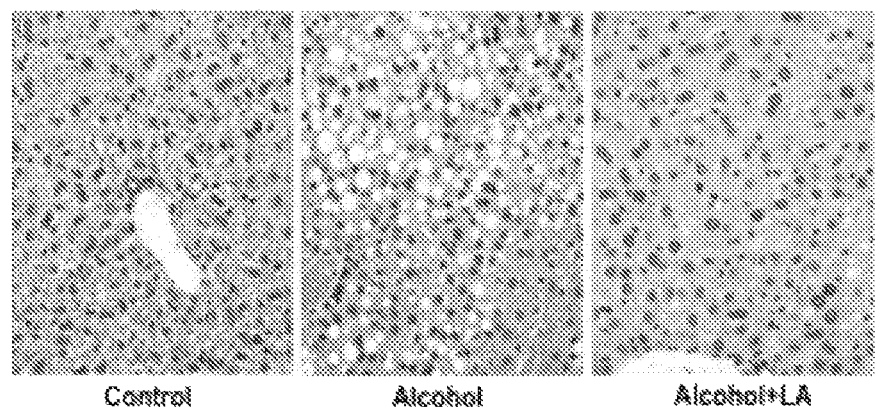

FIG. 32. *L. acidophilus* inhibits ethanol feed and binge (F+B)-induced effects. (A) Oral administration of *L. acidophilus* ($10^9$ CFU/ml) inhibited the ethanol feed and binge (F+B)-induced increase in mouse intestinal permeability. (B) Ethanol F+B caused a marked decrease in mouse intestinal epithelial apical membrane expression and localization of TLR2 (red, upper right panel). *L. acidophilus* treatment caused a marked enhancement of TLR2 expression (lower left panel). *L. acidophilus* also maintained TLR2 localization and expression following ethanol F+B (lower right panel). (C) *L. acidophilus* inhibited alcohol-consumption-induced fatty liver. (D) *L. acidophilus* inhibited alcohol-consumption-induced liver inflammation.

Figure 33:
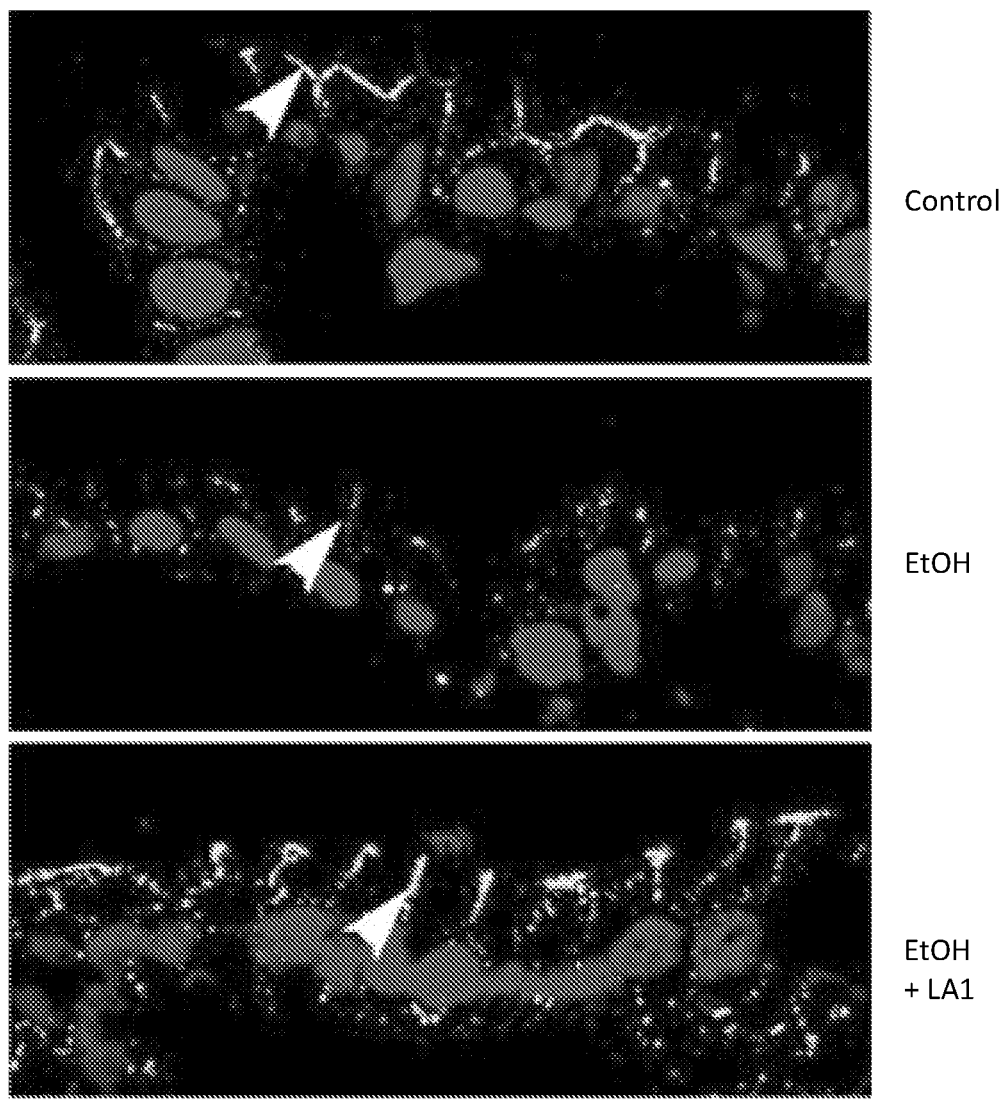

FIG. 33. *L. acidophilus* strain LA inhibited the ethanol-consumption-induced loss of occludin in mouse intestinal epithelial cells. Ethanol feed and binge caused a marked decrease in mouse enterocytes expression of occludin. LA administration caused an enhancement and preservation of enterocyte occludin expression (occludin—green; nucleus—blue).

Figure 34:
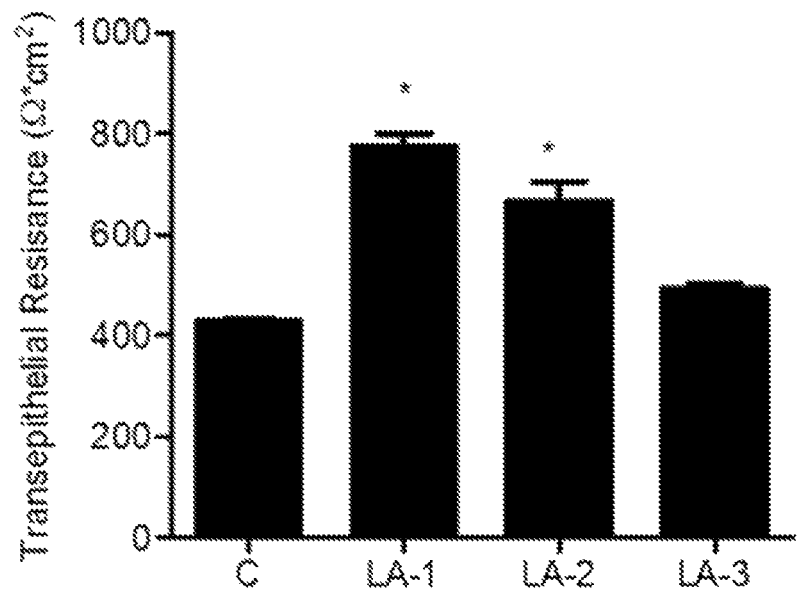

FIG. 34. Effects of three *L. acidophilus* strains on Caco-2 TER. LA1: ATCC 4356; LA2: ATCC BAA-2832; LA3: ATCC 43121).

Figure 35:
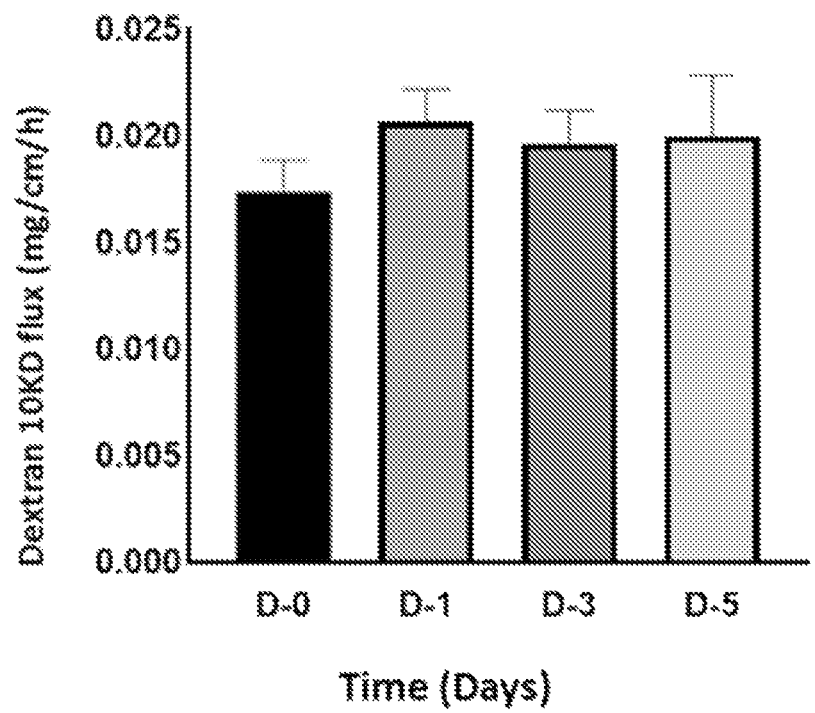

FIG. 35. Effect of oral-gastric administration of *L. acidophilus* strain LA3 (ATCC 43121, $10^9$ CFU/ml) on mouse small intestinal permeability. LA3 did not affect mouse small intestinal permeability. n=3-5 mice.

Figure 36:
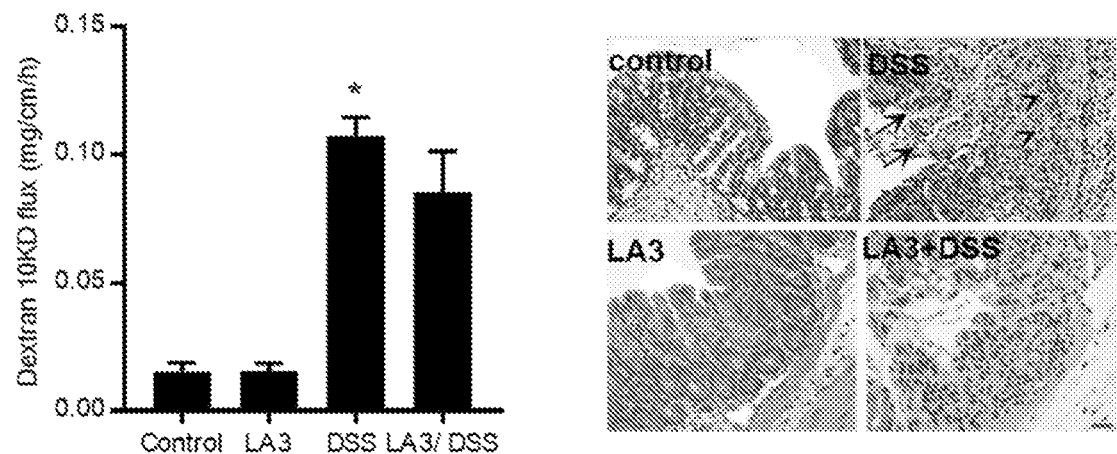

FIG. 36. Effect or oral-gastric administration of *L. acidophilus* strain LA3 (ATCC 43121, $10^9$ CFU/ml) on DSS-induced increase in intestinal permeability and colitis. LA3 administration was started two days before the DSS administration and continued throughout the seven days of daily DSS administration. LA3 did not significantly inhibit the DSS-induced increase in intestinal permeability or the colitis. n=3-5 mice.

Figure 37:
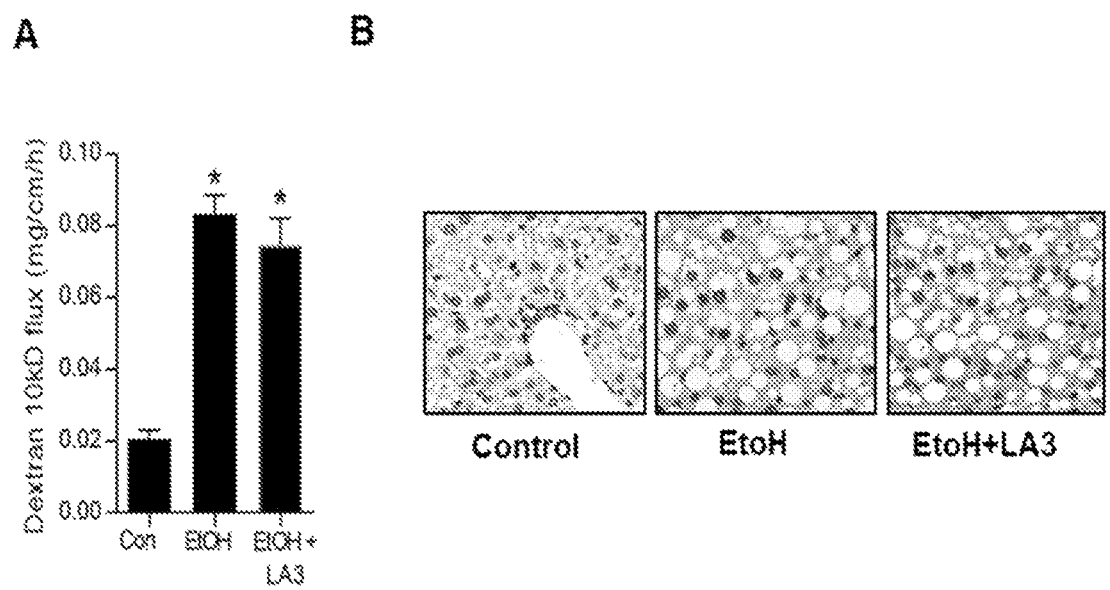

FIG. 37. *L. acidophilus* strain LA3 (ATCC 43121, $10^9$ CFU/ml) failed to inhibit ethanol feed and binge (F+B)-induced effects. (A) Effect of *L. acidophilus* strain LA3 (ATCC 43121, $10^9$ CFU/ml) on ethanol feed and binge (F+B)-induced increase in mouse intestinal permeability. (B) Effect of *L. acidophilus* strain LA3 (ATCC 43121, $10^9$ CFU/ml) on ethanol feed and binge (F+B)-induced alcoholic steatohepatitis. 440×; n=3-5 mice.

DETAILED DESCRIPTION OF ILLUSTRATIVE EMBODIMENTS

Defective intestinal epithelial tight junction (TJ) barrier is a pathogenic factor of inflammatory conditions of the gut such as, for example, inflammatory bowel disease (IBD). Defective intestinal epithelial tight junction barrier allows increased intestinal penetration of bacterial antigens that induce inflammatory response. Intestinal tight junctions provide a physical and functional intercellular barrier against trans-epithelial flux of water soluble molecules or substances in between cells, referred to as paracellular permeability. Similarly, defective intestinal tight junction barrier has also been implicated in the pathogenesis of inflammatory conditions that extend beyond the gut, including alcoholic liver disease. However, there are no currently available therapeutic agents that target the intestinal tight junction barrier. Moreover, the mechanisms that lead to enhancement of intestinal tight junction barrier remain poorly understood. This disclosure describes a new therapeutic composition that targets the intestinal tight junction barrier. In preliminary studies, over 30 probiotic bacterial strains were screened to identify two strains, Lactobacillus acidophilus (ATCC 4356) and Bifidobacterium bifidum (ATCC 35914), that can enhance intestinal tight junction barrier and exhibit therapeutic efficacy in animal models of IBD and liver disease. The two strains when added in combination also work in synergistic manner to cause even greater enhancement in intestinal epithelial tight junction barrier function.

L. acidophilus (LA) and/or B. bifidum (BB) enhancement of the intestinal tight junction barrier is regulated, at least in part, by pathogen recognition receptor TLR2 (Toll-like receptor 2) and/or by Nod1 (nucleotide-binding oligomerization domain containing protein 1) signal transduction pathways. L. acidophilus and/or B. bifidum binding to the apical membrane TLR2 receptor complex activates TLR2 and/or Nod1 signal transduction pathway, which then leads to the activation of occludin (OCLN) gene and an increase in occludin protein expression, a 65-kDa, 522 amino acid integral plasma-membrane protein located at the tight junctions. This disclosure establishes that certain strains of L. acidophilus and/or B. bifidum induce a rapid increase in focal aggregation and localization of TLR2 at the apical membrane, expression of TLR2, and a cytoplasmic-to-apical membrane translocation of Nod1 in intestinal epithelial cells in vivo and in vitro (FIG. 1-4). L. acidophilus-induced augmentation of intestinal tight junction barrier is regulated, at least in part, by its interaction with the TLR2 receptor complex. Moreover, L. acidophilus and/or B. bifidum activation of TLR2 leads to a suppression of NF-κB and activation of the p38 kinase pathway. NF-κB is a pro-inflammatory mediator known to induce tight junction opening and activate inflammatory response. Activation of the p38 kinase pathway causes occludin gene expression, leading to occludin-dependent enhancement in intestinal tight junction barrier.

As indicated above, a defective intestinal tight junction barrier is a pathogenic factor of intestinal inflammation in IBD. Clinical studies in IBD patients show that a persistent increase in intestinal permeability is predictive of poor clinical outcome, and that normalization of intestinal permeability correlates with a sustained long-term clinical remission. Similarly, in animal models of IBD, the increase in intestinal permeability preceded the development of intestinal inflammation and therapeutic enhancement of intestinal tight junction barrier inhibited the development of intestinal inflammation. However, there are no available drugs or therapeutic agents that target the intestinal tight junction barrier.

This disclosure describes methods that involve using L. acidophilus and/or B. bifidum (independently or in combination) as a novel therapeutic agent that targets the intestinal tight junction barrier by its interaction with apical membrane TLR2 and inhibits inflammation of the intestine, liver, and other organs. L. acidophilus and B. bifidum are widely used probiotic bacteria that have no known safety concerns and, thus, can be rapidly advanced to clinical trials.

L. acidophilus and B. bifidum Induce an Enhancement of Caco-2 Tight Junction Barrier Via TLR2-Dependent Dependent Mechanism To identify probiotic bacterial strains that can enhance the intestinal epithelial tight junction (TJ) barrier, over 30 strains of probiotic microbes were examined at increasing bacterial concentrations ($10^8$ cfu/ml, $10^9$ cfu/ml, $10^{10}$ cfu/ml). The intestinal epithelial tight junction barrier was determined in vitro in an established cell culture model system consisting of human-derived intestinal epithelial cell line Caco-2 cells. The Caco-2 cells were grown in permeable insects and allowed to mature into a differentiated, columnar epithelium having the barrier and transport characteristics of intestinal epithelial cells. The tight junction barrier function was determined by measuring transepithelial electrical resistance and apical-to-basolateral flux of paracellular markers inulin or dextran in permeable insert or filter grown Caco-2 monolayers.

Of all the bacterial strains tested, only L. acidophilus and B. bifidum caused a marked enhancement in Caco-2 tight junction barrier function as evidenced by a 60-100% increase in transepithelial electrical resistance (TER) and a 40-60% decrease in transepithelial flux of paracellular marker inulin (FIG. 5, FIG. 6). The time-course of L. acidophilus (ATCC4356) effect on Caco-2 TER and paracellular permeability (trans-epithelial flux of inulin) is shown in FIG. 5. LA ($1\times10^8$ CFU/ml) caused about a 70-80% increase in TER by Day 1, which persisted up to Day 7 (FIG. 5.) Conversely, L. acidophilus caused a 40% decrease in paracellular flux of inulin by Day 1 which also continued up to Day 7 (FIG. 5). Collectively, these data suggested that LA causes a rapid and persistent enhancement of Caco-2 tight junction barrier function. As shown in FIG. 7, other probiotics tested including L. johnsoni, L. rhamnosus, L. brevis, L. casei, L. plantarum, B. breve, and B. infantis ($1\times10^8$ CFU/ml) either did not have any effect or caused a modest or a transitory increase in Caco-2 tight junction barrier function. B. bifidum (ATCC 35914) also caused a marked enhancement in Caco-2 tight junction barrier function as evidenced by an 80% increase in TER and a 50% decrease in inulin flux (FIG. 6).

Pattern recognition receptors (PRRs) are involved in innate immunity by recognizing pathogen-associated molecular patterns (PAMPs). The Toll-like receptors (TLRs) TLR2, TLR4, and TLR5 are plasma-membrane-bound PRRs on intestinal epithelial cells and recognize extracellular PAMPs and play a critical role in the innate immune response. In the following studies, the effect of L. acidophilus on expression of TLR2, TLR4, and TLR5 in filter-grown Caco-2 monolayers was determined. L. acidophilus ($1\times10^8$ CFU/ml) caused an increase in TLR2 protein expression (FIG. 8A), but not TLR4 or TLR5 expression (FIG. 8A), suggesting that TLR2 may be involved in L. acidophilus-induced enhancement of Caco-2 tight junction barrier function. L. acidophilus also caused an increase in TLR2 mRNA expression as assayed by real-time PCR (FIG. 8B), suggesting that the L. acidophilus-induced increase in TLR2 protein expression was due to an increase in TLR2 transcription. To determine the involvement of TLR2 in L. acidophilus-induced enhancement of Caco-2 tight junction barrier function, the effect of small interference RNA (siRNA)-induced knock down of TLR2 expression on L. acidophilus-induced increase in Caco-2 TER was determined. TLR2 siRNA transfection caused a near-complete knock-down of TLR2 in filter-grown Caco-2 monolayers (FIG. 8C). The siRNA induced knock-down of TLR2 expression completely inhibited the *L. acidophilus*-induced increase in Caco-2 TER (FIG. 8D). On the other hand, the siRNA-induced knock down of TLR4 or TLR5 did not inhibit the *L. acidophilus*-induced increase in Caco-2 TER (FIG. 8E). These data indicated that the *L. acidophilus* enhancement of Caco-2 tight junction barrier function was mediated through a TLR2-dependent mechanism.

TLR2 dimerizes with TLR1 or TLR6 to initiate the signal transduction process. The TLR2 complex exists as a TLR2/TLR6 or TLR2/TLR1 heterodimer. TLR6 and TLR2 subunits recognize diacyl and triacyl lipoproteins on the bacterial cell surface, respectively. Therefore, in the following studies, the involvement of TLR1 and TLR6 in the *L. acidophilus* effect was determined. *L. acidophilus* caused an increase in TLR1 and TLR6 protein expression, as shown in FIG. 9A. The requirement of TLR1 or TLR6 in *L. acidophilus*-induced enhancement of Caco-2 tight barrier function was validated by selectively knocking down the expression of TLR1, TLR6, or both by siRNA transfection of filter-grown Caco-2 monolayers. The siRNA-induced knock down of TLR1 or TLR6 partially inhibited the *L. acidophilus*-induced increase in Caco-2 TER (FIG. 9B). However, knocking down both TLR1 and TLR6 completely inhibited the *L. acidophilus*-induced increase in Caco-2 TER (FIG. 9B). These data further validated the involvement of TLR2 heterodimer complex in mediating the *L. acidophilus* enhancement of Caco-2 tight junction barrier function.

*L. acidophilus* or *B. bifidum* Attaches to the Intestinal Epithelial Cells in a TLR2-Dependent Mechanism The conventional scientific paradigm is that Nod1 is a cytoplasmic pattern recognition receptor (PRR) and that TLR2 is a plasma membrane PRR. In response to pathogen associated molecular patterns (PAMPs), TLR2 and/or Nod1 signal transduction pathways are activated to initiate a biological response. The intracellular localization of TLR2 and NOD1 along the apical-to-basal axis (x-z plane) in mature, differentiated Caco-2 monolayer was examined by immunostaining and confocal imaging. In the control Caco-2 monolayers (FIG. 3A), TLR2 was localized in the apical membrane surface and Nod1 was present diffusely in the cytoplasm. *L. acidophilus* caused a rapid aggregation of TLR2 into discrete, focal aggregates (FIG. 3B). This was accompanied by an increase in apical membrane expression of TLR2. *L. acidophilus* attachment to Caco-2 apical membrane only occurred at points of high density TLR2 aggregates (FIG. 3D), suggesting a direct attachment of *L. acidophilus* at the sites of dense TLR2 aggregates. There was also a rapid cytoplasmic-to-apical membrane translocation of Nod1 (FIG. 3B). The apical membrane localization of Nod1 coincided precisely with the TLR2 localization, suggesting a TLR2-dependent Nod1 membrane recruitment process. The siRNA knockdown of TLR2 inhibited the apical membrane translocation of Nod1 (FIG. 3C), confirming that TLR2 was required for the Nod1 membrane targeting.

*B. bifidum* also caused a similar increase in TLR2 apical membrane aggregation, expression, and cytoplasmic-to-apical membrane translocation of Nod1 (FIG. 4). *B. bifidum* attachment to Caco-2 apical membrane also only occurred at points of high density TLR2 localization (FIG. 4D), suggesting attachment of *B. bifidum* at the sites of TLR2 apical membrane aggregation.

Together, these data suggest that the probiotic bacterial enhancement of intestinal tight junction barrier mediated by *L. acidophilus* or *B. bifidum* involves lipopeptide interaction and attachment to the TLR2 receptor complex and activation of TLR2 signal transduction pathway. In the absence of TLR2 interaction, there is no intestinal tight junction barrier enhancement.

*L. acidophilus* and *B. bifidum* Activation of Intracellular Signaling Pathways A down-stream intracellular target of TLR2 and Nod1 signal transduction pathway is the activation of transcription factor NF-κB. Nod1 is also known to activate MAP kinases. To assess the signaling pathways involved, the *L. acidophilus* or *B. bifidum* effect on Caco-2 cells NF-κB activation and MAP kinases was examined. Surprisingly, neither *L. acidophilus* nor *B. bifidum* caused activation of NF-κB, as assessed by inhibitory κB (IκB) degradation (FIG. 10) or NF-κB nuclear translocation (FIG. 11, FIG. 12). This is a novel finding as the current scientific paradigm dictates that the TLR2 and NOD1 signal transduction pathways target NF-κB activation. Rather, *L. acidophilus* and *B. bifidum* caused activation of p38 kinase (FIG. 13, FIG. 15) and JNK but not ERK1/2 (data not shown) as assessed by kinase phosphorylation. To determine the possible involvement of p38 kinase, JNK, and ERK1/2 in *L. acidophilus*/Nod1 or *B. bifidum*/Nod1 enhancement of Caco-2 tight junction barrier, the effect of pharmacologic inhibitors was determined. The p38 kinase inhibitor SB-203580 (Calbiochem, Billerica, MA) inhibited the *L. acidophilus* or *B. bifidum* increase in Caco-2 transepithelial electrical resistance (FIG. 14, FIG. 15), but inhibitors of JNK (SP-600125, Calbiochem, EMD Millipore, Billerica, MA) and ERK1/2 (PD98059, Calbiochem, EMD Millipore, Billerica, MA) did not (data not shown). These results suggested that the p38 kinase signaling pathway was involved in *L. acidophilus*/TLR2 and *B. bifidum*/TLR2 enhancement of Caco-2 tight junction barrier.

*L. acidophilus* or *B. bifidum* Suppresses TNF-α Activation of NF-κB

To explore the possibility that *L. acidophilus* and/or *B. bifidum* suppresses NF-κB activation, the *L. acidophilus* and/or *B. bifidum* effect on TNF-α-induced activation of NF-κB was determined. TNF-α caused a rapid degradation of IκB and nuclear translocation of NF-κB in Caco-2 monolayers (FIGS. 10-12). Both *L. acidophilus* and *B. bifidum* inhibited the TNF-α-induced activation of NF-κB (FIGS. 10-12). The siRNA-induced knockdown of Nod1 reversed the *L. acidophilus* or *B. bifidum* inhibition of NF-κB activation (FIG. 6, FIGS. 10-12), indicating that Nod1 was involved in NF-κB suppression. These results indicated that both *L. acidophilus* and *B. bifidum* inhibited the TNF-α-induced NF-kB activation. These findings show that each of *L. acidophilus* and *B. bifidum* suppresses NF-kB via TLR2/Nod1 signaling pathways.

*L. acidophilus* and *B. bifidum* Cause an Increase in Occludin Expression

To ascertain the mechanism of *L. acidophilus* and/or *B. bifidum* augmentation of intestinal tight junction barrier, the effect of *L. acidophilus* or *B. bifidum* on tight junction protein expression was determined. *L. acidophilus* and *B. bifidum* caused a two-fold to three-fold increase in occludin expression (FIG. 16, FIG. 17) without affecting expression of other tight junction proteins, including ZO-1, claudin-1, claudin-2, claudin-3, claudin-4, and claudin-5 (data not shown). To determine whether the increase in occludin was responsible for the *L. acidophilus* or *B. bifidum* enhancement in Caco-2 tight junction barrier, the effect of siRNA knockdown of occludin on *L. acidophilus* or *B. bifidum* effect on Caco-2 transepithelial electrical resistance was examined. The siRNA knockdown of occludin completely inhibited the *L. acidophilus* or *B. bifidum*-induced increase in Caco-2 transepithelial electrical resistance (FIG. 16, FIG. 17), indicating that the increase in occludin expression was required for the *L. acidophilus* or *B. bifidum* enhancement of Caco-2 tight junction barrier.

*L. acidophilus* and *B. bifidum* Cause an Increase in Occludin Gene Activity Via p38 Kinase Signaling Pathway The effects of *L. acidophilus* and *B. bifidum* on occludin gene activity was assessed by measuring occludin promoter activity and gene transcription. Occludin mRNA expression and promoter activity were determined by real-time PCR and by transfecting Caco-2 cells with plasmid vector encoding the occludin promoter region. A 2,023 bp occludin promoter region was cloned into PGL-3 basic plasmid vector having luciferase as a reporter gene, and the plasmid vector encoding the promoter region was transfected into filter-grown Caco-2 cells[48]. Each of *L. acidophilus* and *B. bifidum* caused a rapid increase in occludin promoter activity, as measured by luciferase activity. *L. acidophilus* and *B. bifidum* also caused an increase in mRNA expression (FIG. 18, FIG. 19). To determine the role of p38 kinase pathway in *L. acidophilus*-induced increase in occludin promoter activity or mRNA expression, the effects of p38 kinase knockdown were examined. The siRNA knockdown of p38 kinase inhibited both the *L. acidophilus* and *B. bifidum*-induced increase in occludin promoter activity and mRNA expression (FIG. 20, FIG. 21), suggesting that *L. acidophilus* or *B. bifidum* activation of occludin gene expression is mediated by the p38 kinase signaling pathway. These results suggested that the increase in occludin protein expression was due to the increase in occludin gene expression.

*L. acidophilus* or *B. bifidum* Oral-Gastric Administration Causes an Enhancement in Mouse Intestinal Epithelial Barrier In Vivo The effect of *L. acidophilus* or *B. bifidum* administration via oral-gastric gavage on mouse intestinal epithelial tight junction barrier function or intestinal permeability was determined in vivo in live mouse by recycling perfusion of 6 cm segment of small intestine or the entire length of the colon. The time-course effect of *L. acidophilus* ($1\times10^9$ cfu/ml) or *B. bifidum* ($1\times10^9$ cfu/ml) administered daily via oral-gastric gavage on mouse intestinal permeability was determined in vivo over the five-day treatment period. Either *L. acidophilus* or *B. bifidum* caused a significant decrease in mouse small intestinal permeability to dextran-10 kDa (a well-established paracellular marker) by Day 1 of *L. acidophilus* or *B. bifidum* administration, which continued up to Day 5 (FIG. 22). The *L. acidophilus* or *B. bifidum* effect on intestinal barrier persisted up to at least six weeks of therapy (data not shown). The *L. acidophilus* or *B. bifidum* treatment for control also caused a significant increase in intestinal tissue electrical resistance (39.1±2.3 for control versus 61.0±2.4 for *L. acidophilus* and 58.6±1.2 for *B. bifidum* treatment; n=4) $\Omega \cdot cm^2$ as determined by intestinal tissue mounting in Ussing chamber. These results showed that each of *L. acidophilus* and *B. bifidum* causes an increase in intestinal epithelial tight junction barrier function (or a decrease in intestinal permeability) in live mice.

*L. acidophilus* Enhancement of Mouse Intestinal Barrier In Vivo is Mediated by an Increase in TLR2 Expression/Activity The requirement of TLR2 expression in mediating the *L. acidophilus*-induced enhancement of mouse intestinal epithelial barrier was also determined. *L. acidophilus* ($1\times10^9$ cfu/ml) oral-gastric administration caused a marked increase in mouse enterocyte apical membrane expression and intestinal tissue TLR2 protein expression (FIG. 22B, FIG. 32B). Next, the effect of *L. acidophilus* on TLR2 knockout (TLR2$^{-/-}$) mice (transgenic mice lacking TLR2 gene and protein) was examined. *L. acidophilus* ($1\times10^9$ cfu/ml) did not cause a decrease in intestinal permeability in TLR2$^{-/-}$ mice (FIG. 22C), confirming that *L. acidophilus*/TLR2 interaction was necessary for the *L. acidophilus*-induced enhancement of mouse intestinal barrier function (or a decrease in intestinal permeability).

*L. acidophilus* or *B. bifidum* Administration Causes Apical Membrane Translocation of Nod1 in Mouse Enterocytes and Increase in Occludin Expression In control mice, Nod1 and Nod2 were present diffusely in the mouse enterocyte cytoplasm in the mucosal surface of mouse intestinal tissue (FIG. 1). *L. acidophilus* or *B. bifidum* oral-gastric gavage administration caused a rapid cytoplasmic-to-apical membrane translocation of enterocyte Nod1 in both the small intestine and the colon (FIG. 4, FIG. 2), corresponding to an increase in apical membrane localization and expression of TLR2 (FIG. 32B). *L. acidophilus* or *B. bifidum* also caused an increase in intestinal tissue expression of occludin (FIG. 24, FIG. 25). The selective in vivo siRNA knockdown of occludin in intestinal epithelial cells covering the intestinal mucosal surface in live mice inhibited the *L. acidophilus*-induced or *B. bifidum*-induced decrease in mouse intestinal permeability (FIG. 24, FIG. 25). These results indicate that the enhancement of mouse intestinal barrier in vivo by *L. acidophilus* or *B. bifidum* was also associated with an increase in apical membrane expression and localization of TLR2 and Nod1 and requires an increase in mouse intestinal epithelial cell occludin expression.

*L. acidophilus* and/or *B. bifidum* Inhibit Dextran Sodium Sulfate (DSS)-Induced Increase in Intestinal Permeability and Intestinal Inflammation Dextran sodium sulfate (DSS) induced colitis in mice is one of the most commonly used animal model of intestinal inflammation. Oral DSS treatment causes a time-dependent increase in colonic permeability and colitis. DSS causes an increase in intestinal permeability by Day 1 and histologic evidence of colitis by Day 5 and more severe colitis by Day 7. *L. acidophilus* or *B. bifidum* administration daily starting two days prior to DSS treatment and continuing concurrently during the seven days of DSS treatment inhibited the DSS-induced increase in colonic permeability and also inhibited the development of colitis (FIG. 26, FIG. 27).

The combined effects of *B. bifidum* and *L. acidophilus* on DSS induced increase in colonic permeability was also examined. The combination caused a significantly greater inhibition on DSS induced increase in colonic permeability and colitis than either probiotic agent alone (FIG. 28). These results suggested that the combined effects of *B. bifidum* and *L. acidophilus* on intestinal barrier preservation and mucosal maintenance were greater than either individual strain alone. The therapeutic efficacy of probiotic bacteria on healing of the inflamed mouse colon was also determined by inducing DSS-induced colitis by DSS treatment for five days, followed by three days of *B. bifidum* oral administration. *B. bifidum* was added starting on Day 5 together with continued DSS administration for up to Day 8. *B. bifidum* treatment caused a decrease in intestinal permeability and a therapeutic healing of the inflamed colonic mucosal surface (FIG. 27A, FIG. 27B; "BB, post-DSS").

*L. acidophilus* and *B. bifidum* Inhibits Loss of Intestinal Barrier and Intestinal Inflammation in IL-10$^{-/-}$ Mice IL-10$^{-/-}$ mice grown in a normal microbial environment typically develop spontaneous enterocolitis. The intestinal permeability measurements in IL-10$^{-/-}$ mice grown in normal microbial housing environment showed a progressive increase in intestinal permeability by 3-4 weeks of normal microbial exposure, which progressed up to 8-10 weeks (data not shown). IL-10$^{-/-}$ mice developed early enterocolitis by 5-6 weeks and more severe inflammation by 8-10 weeks. *L. acidophilus* or *B. bifidum* administration daily for 6 weeks inhibited the increase in intestinal permeability (FIG. 29) and the development of intestinal inflammation (FIG. 30) in IL-10$^{-/-}$ mice raised in normal microbial environment.

*L. acidophilus* Inhibits Alcoholic-Consumption-Induced Increase in Mouse Intestinal Permeability, Fatty Liver and Liver Inflammation (Steatohepatitis)

Patients with alcoholic liver disease (ALD) have an increase in intestinal permeability and the defective intestinal tight junction barrier has been implicated as a pathogenic factor of the liver disease by allowing luminal bacteria or bacterial antigen to permeate across the intestinal barrier and to cause liver inflammation. Individuals suffering from alcoholism who do not develop liver disease have normal intestinal permeability. Thus, defective intestinal tight junction barrier or increase in intestinal permeability has been postulated to play a central role in the pathogenesis of liver disease by allowing bacterial antigenic penetration which, in turn, leads to the liver injury. In the mouse model of alcoholic liver disease, consumption of daily alcohol for 10 days (5% v/v, 1 ml) followed by an alcohol binge (5 g/kg body weight) leads to fatty liver formation and liver inflammation or steatohepatitis, consistent with the findings in alcoholic hepatitis in humans. Using the mouse model of alcoholic liver disease, daily oral administration of alcohol followed by an alcohol binge causes a marked increase in intestinal permeability, gross and histological fatty liver and liver inflammation (characterized by an increase in PMN infiltrate), and elevation in the liver enzyme alanine aminotransferase (ALT) (FIG. 31).

Oral administration of *L. acidophilus* inhibited the alcohol-induced increase in mouse intestinal permeability (FIG. 32A) and alcohol-induced steatohepatitis or liver injury (FIG. 32C, D). Alcohol consumption caused a marked depletion of TLR2 on mouse enterocyte membrane. *L. acidophilus* treatment, however, enhanced apical membrane localization and expression of TLR2, inhibited the alcohol-induced depletion of TLR2, and maintained TLR2 membrane expression in mouse enterocytes following alcohol consumption (FIG. 32B). Alcohol administration also caused a marked depletion of tight junction protein occludin in intestinal epithelial cells covering the mouse small intestinal mucosal surface (FIG. 33). *L. acidophilus* administration inhibited the alcohol-induced depletion of occludin in mouse enterocytes.

Together, these data demonstrate that administering *L. acidophilus* inhibits alcohol-consumption-induced loss of mouse enterocyte membrane TLR2, depletion of tight junction protein occludin, increase in mouse intestinal permeability, and the development of fatty liver and liver inflammation.

*L. acidophilus* and *B. bifidum* Induced Enhancement of Intestinal Epithelial Barrier is Strain Specific To determine whether the *L. acidophilus* and *B. bifidum* induced enhancement of intestinal epithelial tight junction barrier is a species-wide or a strain-specific effect, the effects of different strains of *L. acidophilus* and *B. bifidum* species on Caco-2 TER were examined. The effects of three different *L. acidophilus* strains (LA1, ATCC 4356 (Scav); LA2, ATCC BAA-2832 (LAC-261); LA3, ATCC 43121 (RP32)) on Caco-2 TER were examined. As shown above, LA1 (ATCC 4356) caused about an 80% increase in Caco-2 TER (FIG. 5), LA2 caused about a 40-50% increase in Caco-2 TER, and LA3 did not have any significant effect on Caco-2 TER measurement (FIG. 34). The effects of three different *B. bifidum* strains (BB1, ATCC 35914 (VIII-210); BB2, ATCC 11863 (212A); BB3, ATCC 15696 (S28a)) on Caco-2 TER were also examined. As shown above in FIG. 6, BB1 (ATCC 35914) caused about an 80% increase in Caco-2 TER. BB2 caused about a 10% increase in Caco-2 TER and BB3 did not have any significant effect on Caco-2 TER (not shown), confirming that the BB1 enhancement of intestinal epithelial barrier was also strain-specific.

The whole genome shotgun sequencing performed on the three distinct *L. acidophilus* strains authenticated that the three strains were indeed within the *L. acidophilus* species, with over 98% sequence similarity. These data demonstrated that different bacterial strains within the *L. acidophilus* species have differing effects on intestinal epithelial tight junction barrier: LA1 caused a marked enhancement in Caco-2 tight junction barrier function, LA2 had an intermediate effect, and LA3 had no effect. The effects on in vivo mouse intestinal permeability of intestinal epithelial barrier enhancing strain (LA1) versus the strain without any effect on Caco-2 tight junction barrier (LA3) were investigated. As shown above, oral-gastric administration of LA1 ($1 \times 10^9$ cfu/ml) caused a rapid decrease in intestinal permeability to dextran by Day 1 that persisted up to at least six weeks of treatment (FIG. 22). In contrast, oral-gastric administration of LA3 ($1 \times 10^9$ cfu/ml) did not decrease mouse intestinal permeability (FIG. 35), indicating that LA1 causes an enhancement while LA3 has no effect on mouse intestinal barrier function or intestinal permeability. Moreover, LA3 did not affect apical membrane localization or expression of TLR2, further substantiating the requirement of probiotic/TLR2 interaction for the enhancement of the intestinal barrier function.

Effect of LA1 and LA3 on DSS-Induced Colitis and Alcohol Induced Liver Disease.

The effects of LA3 on DSS-induced increase in mouse intestinal permeability and colitis was examined. As shown above, LA1 inhibited the DSS-induced increase in intestinal permeability and colitis (FIG. 26). In contrast, LA3 did not have significant effect on DSS-induced increase in intestinal permeability or development of colitis (FIG. 36). Next, the effects of LA3 on alcohol-consumption-induced fatty liver and liver inflammation (or steatohepatitis) were examined. Mice were orally administered LA3 daily starting five days prior to alcohol administration and continued throughout the entire alcohol feeding and binge period. LA3 did not inhibit the alcohol induced increase in intestinal permeability or the development of steatohepatitis (FIG. 37).

In contrast, LA1 oral administration completely inhibited the alcohol-consumption-induced increase in intestinal permeability and the development of fatty liver and steatohepatitis (FIG. 32). The LA1 treatment completely inhibited the alcohol induced fatty liver and the liver inflammatory response, demonstrating its therapeutic/prophylactic effect against alcohol induced fatty liver and liver inflammation.

Thus, in one aspect, this disclosure describes a composition for treating subjects having or at risk of having defective intestinal barrier or increased intestinal permeability or increased intestinal epithelial tight junction permeability compared to a normal subject. Generally, the composition includes an amount of a probiotic microbe of the *Lactobacillus* genus. and/or *Bifidobacterium* genus effective to decrease intestinal permeability in the subject. In some embodiments the probiotic *Lactobacillus* genus can include, for example, *L. acidophilus*, *L. rhamnosus*, and/or *L. plantarum*. In particular embodiments, the *Lactobacillus* genus can include, for example, *L. acidophilus*. As used herein, *Lac-* tobacillus genus refers to naturally-occurring species of a *Lactobacillus* genus as well as strains that may be genetically modified to include one or more heterologous coding regions (i.e., include one or more coding regions non-native to the *Lactobacillus* spp) and/or reflect a deletion or modification of one or more endogenous coding regions. In certain embodiments, the *Lactobacillus* spp. can be *L. acidophilus* strain ATCC 4356 (Scav). In other embodiments, the *Bifidobacterium* spp. can be *Bifidobacterium bifidum* strain ATCC 35914.

As used herein, "at risk" refers to a subject that may or may not actually possess the described risk. Thus, for example, a subject "at risk" for developing a specified condition is a subject that possesses one or more indicia of increased risk of having, or developing, the specified condition compared to individuals who lack the one or more indicia, regardless of whether the subject manifests any symptom or clinical sign of having or developing the condition. For example, a subject "at risk" of infection by a microbe is a subject present in an area where individuals have been identified as infected by the microbe and/or is likely to be exposed to the microbe even if the subject has not yet manifested any detectable indication of infection by the microbe and regardless of whether the subject may harbor a subclinical amount of the microbe.

In some embodiments, the composition can further include a second probiotic microbe or a multiple microbe combination. The second probiotic microbe may be a *Bifidobacterium* genus such as, for example, *B. bifidum*, *B. bifidum*, *B. breve*, *B. infantis*, *B. lactis*, and *B. longum*. In particular embodiments, the *Bifidobacterium* genus can include, for example, *B. bifidum*. As used herein, *Bifidobacterium* genus refers to naturally-occurring species of a *Bifidobacterium* genus as well as strains that may be genetically modified to include one or more heterologous coding regions (i.e., include one or more coding regions non-native to the *Bifidobacterium* spp.) and/or reflect a deletion or modification of one or more endogenous coding regions. In certain embodiments, the *Bifidobacterium* spp. can be *B. bifidum* strain VIII-210 (ATCC 35914).

The composition described herein may be formulated in a composition along with a "carrier." As used herein, "carrier" includes any solvent, dispersion medium, vehicle, coating, diluent, isotonic agent, absorption delaying agent, buffer, carrier solution, suspension, colloid, and the like. The use of such media and/or agents for pharmaceutical active substances is well known in the art. Except insofar as any conventional media or agent is incompatible with one or more of the probiotic microbes in the composition, its use in the therapeutic compositions is contemplated. Supplementary active ingredients also can be incorporated into the compositions.

By "pharmaceutically acceptable" is meant a material that is not biologically or otherwise undesirable, i.e., the material may be administered to an individual along with probiotic microbe or microbes in the composition without causing any undesirable biological effects or interacting in a deleterious manner with any of the other components of the pharmaceutical composition in which it is contained.

The composition may be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A composition can be administered to a mucosal surface, such as by administration to, for example, the nasal or respiratory mucosa (e.g., by spray or aerosol). A composition also can be administered via a sustained or delayed release, a microsphere, or a nanoparticle.

Thus, composition may be provided in any suitable form including but not limited to a suspension, an emulsion, a spray, an aerosol, or any form of mixture. The composition may be delivered in formulation with any pharmaceutically acceptable excipient, carrier, or vehicle. For example, the formulation may be delivered in a conventional oral dosage form such as, for example, a dry powder, a tablet, or a capsule. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the one or more probiotic microbes into association with a carrier that constitutes one or more accessory ingredients. In general, a formulation may be prepared by uniformly and/or intimately bringing the probiotic microbe or microbes into association with a liquid carrier, a finely divided solid carrier, or both, and then, if necessary, shaping the product into the desired formulations.

The amount of probiotic microbes administered can vary depending on various factors including, but not limited to, the specific probiotic microbe or microbes in the compositions, the weight, physical condition, and/or age of the subject, and/or the route of administration. Thus, the absolute amount of microbes included in a given unit dosage form can vary widely, and depends upon factors such as the species, age, weight and physical condition of the subject, as well as the method of administration. Accordingly, it is not practical to set forth generally the amount that constitutes an amount of probiotic microbes effective for all possible applications. Those of ordinary skill in the art, however, can readily determine the appropriate amount with due consideration of such factors.

In some embodiments, the method can include administering an amount of the composition to provide a dose of, for example, from about $10^6$ to about $10^{13}$ bacteria per day to the subject, although in some embodiments the methods may be performed by administering the composition in a dose outside this range. In some embodiments, the method includes administering a sufficient amount of the composition to provide a minimum dose of at least $10^6$ bacteria such as, for example, at least $10^6$, at least $5\times10^6$, at least $10^7$, at least $5\times10^7$, at least $10^8$, at least $5\times10^8$, at least $10^9$, at least $5\times10^9$, at least $10^{10}$, at least $5\times10^{10}$, at least $10^{11}$, at least $5\times10^{11}$, at least $10^{12}$, or at least $5\times10^{12}$ bacteria per day. In some embodiments, the method includes administering a sufficient amount of the composition to provide a maximum dose no more than $10^{13}$ bacteria such as, for example, no more than $10^{13}$, no more than $5\times10^{12}$, no more than $10^{12}$, no more than $5\times10^{11}$, no more than $10^{11}$, no more than $5\times10^{10}$, no more than $10^{10}$, no more than $5\times10^9$, no more than $10^9$, no more than $5\times10^8$, no more than $10^8$, no more than $5\times10^7$, no more than $10^7$, or no more than $5\times10^6$, bacteria per day. In some embodiments, the methods may be performed by administering a sufficient amount of the composition to provide a daily dose of bacteria in a range having endpoints defined by any minimum dose listed above and any maximum dose listed above that is greater than the selected minimum dose. Thus, for example, in certain embodiments, the methods may be performed by administering a sufficient amount of the composition to provide from about $5 \times 10^8$ to about $10^{11}$ bacteria per day. In one particular embodiment, the method can include administering an amount of the composition to provide a dose of, for example, from about $10^9$ to about $5 \times 10^{10}$ bacteria per day. In another particular embodiment, the method can include administering an amount of the composition to provide a dose of from about $10^{10}$ to about $3 \times 10^{10}$ bacteria per day.

As used above, the term "bacteria per day" refers to the cumulative amount of bacteria in the composition, regardless of the identity and/or number of probiotic species present in the composition. Thus, an exemplary dose of $10^{10}$ bacteria per day can include, for example, $10^{10}$ *L. acidophilus* bacteria, $10^{10}$ *B. bifidum* bacteria, a mixture of $5 \times 10^9$ *L. acidophilus* bacteria and $5 \times 10^9$ *B. bifidum* bacteria, a mixture of $7 \times 10^9$ *L. acidophilus* bacteria and $3 \times 10^9$ *B. bifidum* bacteria, or a mixture of $4 \times 10^9$ *L. acidophilus* bacteria, $4 \times 10^9$ *B. bifidum* bacteria, and $2 \times 10^9$ of another probiotic species.

In some embodiments, the compositions may be administered, for example, from a single dose to multiple doses per week, although in some embodiments the method can be performed by administering the composition at a frequency outside this range. In certain embodiments, the composition may be administered once per day or, as an alternative, as many times per day as is required to equal the total daily dose.

Thus, in another aspect, this disclosure describes methods that generally involve administering to a subject a composition as described above in an amount effective to provide treatment of a condition. As used herein, the term "treat" or variations thereof refer to reducing, limiting progression, ameliorating, or resolving, to any extent, the symptoms or signs related to a condition. "Ameliorate" refers to any reduction in the extent, severity, frequency, and/or likelihood of a symptom or clinical sign characteristic of a particular condition. "Symptom" refers to any subjective evidence of disease or of a patient's condition. "Sign" or "clinical sign" refers to an objective physical finding relating to a particular condition capable of being found by one other than the patient.

A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after a condition manifests in a subject, while "prophylactic" treatment is initiated before a condition manifests in a subject. Thus, "prophylactic" treatment may be initiated for a subject "at risk" of having a condition.

In some embodiments, the method can include administering to the subject an amount of the composition effective to enhance intestinal barrier function, decrease intestinal permeability, and/or decrease intestinal epithelial tight junction permeability. In another embodiment, the method can include administering to the subject an amount of the probiotic bacterial composition effective to induce an aggregation of TLR2 in apical membrane surface, increase in TLR2 expression, and/or activation of the TLR2 signal transduction pathway in intestinal epithelial cells of the subject. In another embodiment, the method can include administering to the subject an amount of the composition effective to induce cytoplasmic to apical membrane translocation and/or activation of Nod1 in intestinal epithelial cells of the subject. In another embodiment, the method can include administering to subject an amount of the composition effective to induce suppression or inhibition of NF-κB activation in intestinal cells. In another embodiment, the method can include administering to the subject an amount of the composition effective to cause an activation of occludin gene and an increase in occludin expression in intestinal epithelial cells. In another embodiment, the method can include administering to the subject an amount of the composition effective to ameliorate at least one symptom or clinical sign of an inflammatory condition of the gut and/or ameliorate at least one component of intestinal inflammation marker in intestinal tissue or in the serum including endoscopic improvement, histologic improvement, decrease in pro-inflammatory mediators, decrease in inflammatory markers, or decrease in inflammatory cells. In some of these embodiments, the inflammatory condition of the gut can include, for example, irritable bowel syndrome, necrotizing enterocolitis, Crohn's disease, ulcerative colitis, coeliac disease, heat stroke-associated enteritis, and NSAID-associated enteritis. In another embodiment, the method can include administering to the subject an amount of composition effective to ameliorate at least one symptom or clinical signs of inflammatory conditions and/or serological or tissue marker of inflammation that include and/or extend beyond the gut. In some of these embodiments, the inflammatory conditions which include or extend beyond the gut include, for example, alcoholic liver diseases, non-alcoholic fatty liver disease, non-alcoholic steatohepatitis, viral liver diseases, pancreatic diseases, neurological diseases including autism, and cardiac diseases. In another embodiment, the method can include administering to the subject an amount of the composition effective to ameliorate at least one symptom or clinical sign of an inflammatory condition of the liver and/or ameliorate at least one component of intestinal inflammation marker in liver tissue including histologic improvement, improvement or decrease of liver enzymes, decrease in pro-inflammatory mediators, decrease in inflammatory markers, decrease in fatty liver, decrease in immune cell infiltration of the liver, or decrease in inflammatory cells. In another embodiment, the method can include administering to the subject with an intestinal permeability disorder or an increase in intestinal permeability an amount of the composition effective to cause an enhancement of intestinal epithelial barrier function, decrease intestinal permeability and/or decrease intestinal epithelial tight junction permeability.

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLE

Example 1

For a patient with an intestinal disease or an intestinal permeability disorder, a composition that includes *L. acidophilus* (ATCC 4356), *B. bifidum* (ATCC 35914), or combination of *L. acidophilus* (ATCC 4356) and *B. bifidum* (ATCC 35914) is administered orally at a dose of $10^{10}$ bacteria on a daily basis.

The effect of the *L. acidophilus*, *B. bifidum* or the combination administration on intestinal barrier function is measured periodically by assessing intestinal permeability using lactulose and mannitol as the permeability markers and/or by measuring gut-derived bacterial products (such as bacterial endotoxin) and/or bacteria in the circulating blood. The therapeutic effect of probiotic agents on intestinal inflammation is assessed by measuring serum markers of inflammation, endotoxin level, gut-derived bacterial products, endoscopic evaluation of intestinal inflammation, and/or by clinical assessment of signs and symptoms of intestinal inflammation.

Example 2

For a patients with alcoholic liver disease, a composition that includes *L. acidophilus* (ATCC 4356), *B. bifidum* (ATCC 35914), or combination of *L. acidophilus* (ATCC 4356) and *B. bifidum* (ATCC 35914) is administered orally at a dose of $10^{10}$ bacteria on a daily basis.

The effect of the *L. acidophilus*, *B. bifidum* or the combination administration on intestinal barrier function is measured periodically by assessing intestinal permeability using lactulose and mannitol as the permeability markers and/or by measuring gut-derived bacterial products (such as bacterial endotoxin) and/or bacteria in the circulating blood. The therapeutic effect of probiotic agents on alcoholic liver disease is assessed by measuring serum markers of inflammation, endotoxin level, liver function tests, markers of fatty liver, and/or clinical symptoms and signs.

The complete disclosure of all patents, patent applications, and publications, and electronically available material cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising:
   administering to a subject having or at risk of having defective intestinal barrier, increased intestinal permeability and/or epithelial tight junction permeability a composition comprising a combination of *Lactobacillus acidophilus* strain ATCC 4356 and *Bifidobacterium bifidum* in an amount effective to induce an inhibition or suppression of NF-κB activation in intestinal epithelial cells of the subject.

2. A method comprising:
   administering to a subject having or at risk of having increased intestinal permeability and/or epithelial tight junction permeability and/or inflammation a composition comprising a combination of *Lactobacillus acidophilus* strain ATCC 4356 and *Bifidobacterium bifidum* in an amount effective to induce cytoplasmic to apical membrane translocation of Nod1 or activation of Nod1 signal transduction pathway in intestinal epithelial cells of the subject.

3. A method comprising:
   administering to a subject having or at risk of having increased intestinal permeability and/or epithelial tight junction permeability and/or inflammation a composition comprising a combination of *Lactobacillus acidophilus* strain ATCC 4356 and *Bifidobacterium bifidum* in an amount effective to induce an increase in occludin expression in intestinal epithelial cells of the subject.

4. A method comprising:
   administering to a subject having or at risk of having increased epithelial tight junction permeability a composition comprising a combination of *Lactobacillus acidophilus* strain ATCC 4356 and *Bifidobacterium bifidum* in an amount effective to ameliorate at least one symptom or clinical sign of an inflammatory condition of the gut.

5. The method of claim 4, wherein the inflammatory condition of the gut comprises inflammatory bowel disease, Crohn's disease, ulcerative colitis, necrotizing enterocolitis, or coeliac disease.

6. A method comprising:
   administering to a subject having or at risk of having increased intestinal permeability and/or epithelial tight junction permeability a composition comprising a combination of *Lactobacillus acidophilus* strain ATCC 4356 and *Bifidobacterium bifidum* in an amount effective to ameliorate at least one symptom or clinical sign of an inflammatory condition of an organ.

7. The method of claim 6, wherein the organ comprises the liver.

8. A method comprising:
administering to a subject having or at risk of having defective intestinal barrier, increased intestinal permeability and/or epithelial tight junction permeability and/or inflammation a composition comprising a combination of *Lactobacillus acidophilus* strain ATCC 4356 and *Bifidobacterium bifidum* in an amount effective to increase intestinal barrier function, decrease intestinal permeability or decrease intestinal epithelial tight junction permeability and/or decrease intestinal inflammation.

9. The method of claim 1, wherein the composition is administered before the subject exhibits a symptom or clinical sign resulting from increased intestinal permeability or intestinal epithelial tight junction permeability.

10. The method of claim 1, wherein the composition comprises a combination of *L. acidophilus* strain ATCC 4356 and *B. bifidum*, wherein the composition is more effective than a composition comprising either strain without the other strain.

11. The method of claim 2, wherein the composition is administered before the subject exhibits a symptom or clinical sign resulting from increased intestinal permeability or intestinal epithelial tight junction permeability.

12. The method of claim 2, wherein the composition comprises a combination of *L. acidophilus* strain ATCC 4356 and *B. bifidum*, wherein the composition is more effective than a composition comprising either strain without the other strain.

13. The method of claim 3, wherein the composition is administered before the subject exhibits a symptom or clinical sign resulting from increased intestinal permeability or intestinal epithelial tight junction permeability.

14. The method of claim 3, wherein the composition comprises a combination of *L. acidophilus* strain ATCC 4356 and *B. bifidum*, wherein the composition is more effective than a composition comprising either strain without the other strain.

* * * * *